(12) United States Patent
Gray et al.

(10) Patent No.: US 7,972,811 B2
(45) Date of Patent: Jul. 5, 2011

(54) EUKARYOTIC SIGNAL SEQUENCES FOR POLYPEPTIDE EXPRESSION AND POLYPEPTIDE DISPLAY LIBRARIES

(75) Inventors: Jeff Gray, Solano Beach, CA (US); Joe Buechler, Carlsbad, CA (US); Uday Kumar Veeramallu, San Diego, CA (US)

(73) Assignee: XOMA Technology Ltd., Berkeley, CA (US)

( * ) Notice: Subject to any disclaimer, the term of this patent is extended or adjusted under 35 U.S.C. 154(b) by 3 days.

(21) Appl. No.: 12/021,098

(22) Filed: Jan. 28, 2008

(65) Prior Publication Data

US 2010/0009857 A1 Jan. 14, 2010

Related U.S. Application Data

(60) Division of application No. 10/367,169, filed on Feb. 13, 2003, now Pat. No. 7,396,661, which is a continuation-in-part of application No. 10/076,802, filed on Feb. 13, 2002, now Pat. No. 7,094,579.

(51) Int. Cl.
*C12N 1/21* (2006.01)
*C12N 15/74* (2006.01)
*C12P 21/02* (2006.01)
*C12Q 1/68* (2006.01)
*C12Q 1/70* (2006.01)
*C07K 16/18* (2006.01)
*A61K 31/70* (2006.01)

(52) U.S. Cl. ............ 435/69.1; 435/7.1; 435/320.1; 530/387.1

(58) Field of Classification Search ............ None
See application file for complete search history.

(56) References Cited

U.S. PATENT DOCUMENTS

| 5,223,409 | A | 6/1993 | Ladner et al. | |
| 6,545,140 | B1 * | 4/2003 | Harmon et al. | 536/23.5 |
| 6,818,411 | B2 | 11/2004 | Hutchens et al. | |
| 7,094,579 | B2 | 8/2006 | Gray et al. | |
| 7,396,661 | B2 | 7/2008 | Gray et al. | |
| 2008/0214411 | A1 | 9/2008 | Gray et al. | |

FOREIGN PATENT DOCUMENTS

| DE | 202 07 301 U1 | 5/2002 |
| WO | 98/47343 C2 | 10/1998 |
| WO | 00/47741 A1 | 8/2000 |
| WO | 03/068956 A1 | 8/2003 |

OTHER PUBLICATIONS de Hostos, E.L., Schilling, J. and Grossman, A.R. Structure and expression of the gene encoding the periplasmic arylsulfatase of *Chlamydomonas reinhardtii*; Mol. Gen. Genet. vol. 218 (2), pp. 229-239 (1989).*
Score Search Results Details for U.S. Appl. No. 12/021,098 and Search Result Oct. 13, 2009 Result 8.*
Supplementary European Search Report PCT/US03/04791, Dec. 20, 2005 (5 total pages).
Piers, K.L., Brown, M.H., Hancock, R.E.W., Recombinant DNA procedures for producing small antimicrobial cationic peptides in bacteria, Gene 134 (1992) 7-13.
Haldimann, A., Daniels, L.L., Wanner, B.L., Use of New Methods for Construction of Tightly Regulated Arabinose and Rhamnose Promoter Fusions in Studies of the *Escherichia coli* Phosphate Regulon, Journal of Bacteriology, Mar. 1998, pp. 1277-1286.
Humphreys, D.P., Sehdev, M., Chapman, A.P., Ganesh, R., Smith, B.J., King, L.M., Glover, D.J., Reeks, D.G., Stephens, P.E., High-Level Periplasmic Expression in *Escherichia coli* Using a Eukaryotic Signal Peptide: Importance of Codon Usage at the 5' End of the Coding Sequence, Protein Expression and Purification 20, pp. 252-264 (2000).
Georigiou, G., et al, Display of heterologous proteins on the surface of microorganisms: From the screening of combininatorial libraries to live recombinant vaccines. Nature Biotechnology, Jan. 1997; 15:29-34.
Jestin et al., "Improving the display of proteins on filamentous phage", Res. Microbiol 152 (2001) pp. 187-191.
Strobel et al in "Efficient Display of Two Enzymes on Filamentous Phage Using an Improved Signal Sequence" in Molecular Biotechnology, vol. 24, (2003) pp. 1-9.
Fernandez, Luis Angel, "Prokaryotic expression of antibodies and affibodies" in Current Opinion in Biotechnology, Aug. 2004;15:364-373.
Choi and Yee, Secretory and extracellular production of recombinant proteins using *Escherichia coli*, Appl Microbiol Biotechnol (2004) 64:625-635.
Nielsen, Henrik, et al., Identification of prokaryotic and eukaryotic signal peptides and prediction of their cleavage sites, Protein Engineering (1997) 10(1):1-6.
Pines and Inouye, Expression and Secretion of Proteins in *E. coli*, Mol Biotech (1999) 12:25-34.
Michaelson, D. et al: Cationic defensins arise from Charge-neutralized propeptides: a mechanism for avoiding leukocyte autocytotoxicity? J Leukoc Biol 51(6):634-639 (1992).
Extended European Search Report, Application No. 08163005.5 EPO Comm dated Feb. 16, 2009.

* cited by examiner

*Primary Examiner* — Nancy Vogel
*Assistant Examiner* — Catherine Hibbert
(74) *Attorney, Agent, or Firm* — John M. Polo

(57) ABSTRACT

The present invention generally relates to methods and compositions for expressing proteins or polypeptides in prokaryotic hosts using eukaryotic signal sequences.

12 Claims, 2 Drawing Sheets

EUKARYOTIC SIGNAL SEQUENCES FOR POLYPEPTIDE EXPRESSION AND POLYPEPTIDE DISPLAY LIBRARIES

CROSS-REFERENCE TO RELATED APPLICATIONS

This is a divisional application of U.S. patent application Ser. No. 10/367,169, filed Feb. 13, 2003 and issued as U.S. Pat. No. 7,396,661, which is a continuation-in-part of U.S. patent application Ser. No. 10/076,802, filed Feb. 13, 2002 and issued as U.S. Pat. No. 7,094,579, the entire disclosures of which is are hereby incorporated by reference.

FIELD OF THE INVENTION

This invention relates to methods of using specific eukaryotic signal sequences for efficient expression and secretion of polypeptides, particularly in prokaryotic hosts. The invention also relates to methods of using eukaryotic signal sequences to produce and screen polypeptide display libraries.

BACKGROUND OF THE INVENTION

Proteins that are secreted from a cell through a cell membrane are generally produced within the cell in a precursor form, referred to as a "preprotein" that includes an additional peptide sequence at the amino-terminus which is required to assist the protein in traversing the membrane. This additional peptide sequence is referred to as a "signal sequence" or "leader sequence". In prokaryotes such as E. coli, the signal peptides direct secretion of proteins to the periplasm and outermembrane. In eukaryotic cells, preproteins containing a signal sequence are inserted through the membrane of the rough endoplasmic reticulum (RER), thereby directing the preprotein into the secretory pathway. During this process, the signal sequence interacts with a particle called the signal recognition particle (SRP), which in turn is recognized by an RER membrane protein referred to as an SRP receptor or docking protein. After or simultaneous with insertion of the preprotein into the RER, the signal sequence is cleaved from the preprotein by an enzyme called a signal peptidase, thereby releasing the mature protein into the RER. Once proteins are segregated into the lumen of the ER, they migrate to the Golgi apparatus and then to secretory vesicles. Fusion of the secretory vesicles with the plasma membrane releases the contents of vesicle into the extracellular environment. In organisms having both a plasma membrane and a cell wall, e.g., yeast, the vesicle contents typically are released into the periplasmic space between the membrane and the cell wall.

Although signal sequences of secretory proteins share some general features, e.g., typically a short chain amino acid at the carboxyl end and a hydrophobic central region, no uniform consensus sequence exists for the vast array of secreted proteins (see e.g., Watson, M. E. E. (1984) Nucl. Acids. Res. 12:5145-5164). In fact, the primary structure of signal sequences of different secreted proteins vary considerably, both among secreted proteins of the same species and secreted proteins of different species. This suggests that each secreted protein has evolved with a particular signal sequence that is well suited for its own translocation across a cell membrane. In addition to differences in the sequences of their signal peptides, prokaryotes and eukaryotes are also different in the secretion process, e.g., in the function of the signal recognition particle and the use of chaperones.

Different E. coli signal sequences have been shown to be compatible for efficient expression of a heterologous polypeptide in E. coli. However, functional substitution between signal sequences of different species, esp. between prokaryotes and eukaryotes, are unpredictable, problematic, and less efficient. First, a host might successfully express and secret a heterologous protein with its native signal sequence, but may not be able to correctly cleave the signal peptide (e.g., Bacillus α-amylase in E. coli cell; see, e.g., Suominen et al., Microbiol. 141:649-54, 1995). In addition, while a few eukaryotic proteins have been secreted to the E. coli periplasm using their native signal sequences, it has been suggested that most eukaryotic signal sequences cannot function efficiently in a prokaryotic host such as E. coli (see, e.g., Humphreys et al., Prot. Exp. and Purif. 20:252-64, 2000). Some eukaryotic proteins, e.g., human apolipoprotein E, need to have their native signal sequences replaced with a prokaryotic signal in order to be secreted to the E. coli periplasm (see, e.g., Monteilhet et al., Gene 125:223-8, 1993).

The ability to efficiently produce a recombinant protein (e.g., an immunoglobulin) in a secreted form is highly desirable, since the secreted protein can then be recovered from a medium in which the host cells (e.g., E. coli) are growing. As discussed above, this process often does not function to the degree desired, for example because the native signal sequence of the recombinant protein often does not operate well in the host cell. Although certain signal sequences have been identified which may be useful for the secretion of recombinant proteins (e.g., an recombinant immunoglobulin), there is still a need for additional signal sequences that can promote efficient secretion of proteins, including recombinant immunoglobulins in a prokaryotic host. The present invention fulfills this and other needs.

SUMMARY OF THE INVENTION

In one aspect, the present invention provides methods of expressing a Fab fragment. The methods comprise the steps of (i) providing a culture of bacterial cells containing a vector comprising a rhamnose promoter operably linked to a dicistronic transcriptional unit encoding an antibody heavy chain and an antibody light chain each operably linked to a eukaryotic signal sequence; (ii) adding rhamnose to the culture to induce the rhamnose promoter whereby the antibody heavy chain and light chain and their linked signal sequences are expressed, secreted to the periplasm, the signal peptide sequences are processed from the heavy and light chains, and the heavy and light chains assemble to form a Fab fragment which specifically binds to a target molecule; and (iii) recovering the Fab fragment from the culture of bacterial cells. In these methods, each of the eukaryotic signal sequence encodes a signal peptide having the sequence of MRTLAILAAILLVALQAQA (SEQ ID NO:2) or MKILILGIFLFLCSTPAWA (SEQ ID NO:1).

In some of the methods, the signal sequence operably linked to the heavy chain encodes MRTLAILAAILLVALQAQA (SEQ ID NO:2), and the signal sequence operably linked to the light chain encodes MKILILGIFLFLCSTPAWA (SEQ ID NO:1). In some methods, the signal sequence operably linked to the heavy chain encodes MKILILGIFLFLCSTPAWA (SEQ ID NO:1), and the signal sequence operably linked to the light chain encodes MRTLAILAAILLVALQAQA (SEQ ID NO:2). In still some other methods, the signal sequence operably linked to the heavy chain and the signal sequence operably linked to the light chain both encode MKILILGIFLFLCSTPAWA (SEQ ID NO:1) or both encode MRTLAILAAILLVALQAQA (SEQ ID NO:2).

In some of the methods, the host cells for expressing the Fab fragment are *E. coli* rhaB+ cells. In some other methods, the host are *E. coli* rhaB– cells. In some methods, the Fab fragment is recovered from media in the culture. Some of the methods further comprise lysing the cells to release the Fab fragment before the recovering step.

In one aspect, the invention provides improved methods of displaying a Fab fragment from a phage. The methods comprise expressing in bacterial cells a phage display vector encoding heavy and light antibody chains. The light chain is operably linked to a first signal peptide sequence, and the heavy chain is operably linked to a phage outersurface protein and a second signal peptide sequence. In these methods, the antibody chains are expressed, secreted to the periplasm of the cells, and processed to separate the antibody chains from the signal peptide sequences. The antibody chains are then assemble as a Fab fragment displayed from the outersurface of a phage particle. The improvement of the methods resides in that the first and second signal sequences each encodes a eukaryotic signal peptide having the sequence MKILILGIFLFLCSTPAWA (SEQ ID NO:1) or MRTLAILAAILLVALQAQA (SEQ ID NO:2). The first and second signal peptide sequences can be different, e.g., one having the sequence of SEQ ID NO:1 and the other SEQ ID NO:2. Alternatively, both signal peptide sequences can be the same, e.g., both having the sequence of SEQ ID NO:1 or both having the sequence of SEQ ID NO:2.

In another aspect, the invention provides fusion proteins that comprise an antibody chain in operable linkage with a eukaryotic signal peptide sequence. The eukaryotic signal peptide can be MKILILGIFLFLCSTPAWA (SEQ ID NO: 1) or MRTLAILAAILLVALQAQA (SEQ ID NO:2).

In another aspect, the invention provides expression vectors for expressing a polypeptide in a bacterial cell. The vectors comprise a bacterial promoter, a polynucleotide encoding the polypeptide, and a eukaryotic signal sequence operably linked to the polynucleotide. The eukaryotic signal peptide can be MRTLAILAAILLVALQAQA (SEQ ID NO:2) or MKILILGIFLFLCSTPAWA (SEQ ID NO:1). In some of the vectors, the bacterial promoter is an inducible rhamnose promoter.

In still another aspect, the invention provides methods of expressing a polypeptide in a bacterial cell. The methods comprise the steps of (i) providing a culture of bacterial cells containing a vector comprising a rhamnose promoter, a polynucleotide encoding the polypeptide, and a eukaryotic signal sequence operably linked to the polynucleotide; (ii) adding rhamnose to the culture to induce the rhamnose promoter whereby the polynucleotide and the signal sequence are expressed, secreted to the periplasm, and expressed signal peptide sequence is processed from the polypeptide expressed from the polynucleotide; and (iii) recovering the polypeptide from the culture of bacterial cells. In these methods, the eukaryotic signal sequence encodes a signal peptide having the sequence of MRTLAILAAILLVALQAQA (SEQ ID NO:2) or MKILILGIFLFLCSTPAWA (SEQ ID NO:1).

In one aspect, the invention provides methods of expressing polypeptides in host cells. The methods comprise the steps of: (i) providing a culture of the host cells, wherein the host cells comprise a vector comprising a polynucleotide encoding the polypeptide, and wherein the polynucleotide is operably linked to a eukaryotic signal sequence; (ii) expressing the polynucleotide sequence and signal sequence, wherein the polypeptide expressed from the polynucleotide and the expressed signal peptide sequence are secreted, and wherein the expressed signal peptide sequence is processed from the polypeptide expressed from the polynucleotide; and (iii) recovering the polypeptide from the culture of host cells. In these methods, the eukaryotic signal sequences encode a signal peptide having the sequence of MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3).

In another aspect, the invention provides methods of displaying polypeptides from replicable genetic packages. The methods comprise the steps of expressing in a prokaryotic or eukaryotic host cell a polypeptide display vector comprising a polynucleotide encoding the polypeptide, wherein the polynucleotide is operably linked to a eukaryotic signal sequence, whereby the polynucleotide sequence and signal sequence are expressed and secreted, and the expressed signal peptide sequence is processed from the expressed polypeptide, such that the polypeptide is displayed from the outer surface of the replicable genetic package. In these methods, the eukaryotic signal sequences encode a signal peptide having the sequence of MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3).

In another aspect, the invention provides methods of preparing polypeptide display libraries. The methods comprise the steps of introducing a polynucleotide encoding an exogenous polypeptide into the genome of a replicable genetic package to form a fusion protein with an endogenous protein that is normally expressed from the outersurface of the replicable genetic package, wherein the polynucleotide is operably linked to a eukaryotic signal sequence, and expressing the fusion protein, wherein the fusion protein is transported to the outersurface and assembled to display the exogenous polypeptide from the outersurface of the replicable genetic passage. In these methods, the eukaryotic signal sequences encode a signal peptide having the sequence of MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3).

In another aspect, the invention provides cells for expressing polypeptides. The host cells comprise vectors comprising a polynucleotide encoding the polypeptide and a eukaryotic signal sequence operably linked to the polynucleotide. In these host cells, the eukaryotic signal sequences encode a signal peptide having the sequence of MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3).

In still another aspect, the invention provides vectors for expressing polypeptides in a host cell. The vectors comprise polynucleotides encoding the polypeptides, promoters operably linked to the polynucleotides, and eukaryotic signal sequences operably linked to the polynucleotides. The eukaryotic signal sequences encode a eukaryotic signal peptide having the sequence of MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3).

The polypeptides useful in methods, host cells, or vectors according to the invention can be prokaryotic or eukaryotic polypeptides, including antibodies. Antibodies can be whole antibodies or binding fragments thereof, including Fab fragments, Fv fragments or single chain fragments.

Host cells can be prokaryotic, yeast, insect or mammalian tissue host cells. Promoters useful in methods, host cells or vectors according to the invention can be inducible promoters. Preferred host cells are prokaryotic host cells, particularly bacterial cells wherein the promoters are bacterial promoters.

In one aspect, the invention provides methods of selecting eukaryotic signal sequences for expression of polypeptides in bacterial cells, including antibody polypeptides. The methods comprise the steps of (a) culturing bacterial cells containing a polynucleotide encoding a polypeptide, wherein the polynucleotide is operably linked to a rhamnose promoter and to a eukaryotic signal sequence which encodes a signal peptide; (b) expressing the polynucleotide and the signal sequence; (c) testing for expression of the polypeptide and for processing of the signal sequence from the polypeptide by the bacterial cells, and (d) selecting the eukaryotic signal sequence if (i) polypeptide expression is detectable; and (ii) the signal sequence is processed from the polypeptide. Eukaryotic signal sequences are selected according to these methods and are useful for efficient expression and production of polypeptides.

In another aspect, the invention provides additional methods of selecting eukaryotic signal sequences for expression of polypeptides in bacterial cells, including antibody polypeptides. The additional methods comprise the steps of (a) expressing a polypeptide from a polynucleotide encoding a polypeptide, wherein the polynucleotide is operably linked to a first eukaryotic signal sequence which encodes a signal peptide; (b) expressing the polypeptide from the polynucleotide encoding the polypeptide, wherein the polynucleotide is operably linked to a second eukaryotic signal sequence, that is MKILILGIFLFLCSTPAWA (SEQ ID NO: 1), MRTLAILAAILLVALQAQA (SEQ ID NO: 2), or MGALAVFAVACLAAVASVAHA (SEQ ID NO: 3); (c) selecting the eukaryotic signal sequence that is the first eukaryotic signal sequence if (i) the polypeptide expression of step (a) is substantially the same as or greater than the polypeptide expression of step (b); and/or (ii) the first eukaryotic signal sequence of step (a) is processed from the polypeptide substantially the same as or greater than the second eukaryotic signal sequence of step (b). The polynucleotides optionally are operably lined to a rhamnose promoter. Eukaryotic signal sequences are selected according to these additional methods and are useful for efficient expression and production of polypeptides.

A further understanding of the nature and advantages of the present invention may be realized by reference to the remaining portions of the specification, the figures and claims.

All publications, GenBank deposited sequences, ATCC deposits, patents and patent applications cited herein are hereby expressly incorporated by reference in their entirety and for all purposes.

DETAILED DESCRIPTION OF THE INVENTION

I. Overview

Figure 1:
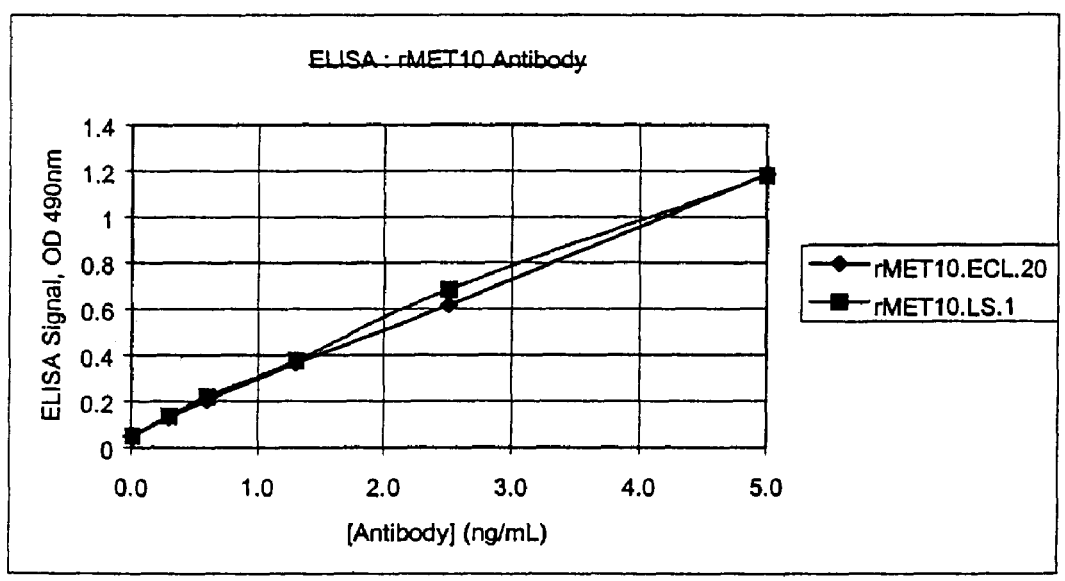
FIG. 1 shows expression of rMET10 antibody in *E. coli* with the same eukaryotic signal sequence on both heavy and light chains.

It is generally unpredictable whether a signal sequence from one species would be functional and/or efficient in another species. This is especially true with respect to functional substitution of signal sequences between prokaryotes and eukaryotes (see, Humphreys et al., supra). Such unpredictability is also demonstrated by the present inventors. Of a total of 19 eukaryotic signal peptides examined, only 3 properly processed and directed efficient expression and secretion of the operably linked polypeptide sequence in a prokaryotic expression system (Examples 2-3).

In accordance with the discovery, the invention provides methods and vectors with general applicability for expressing proteins or polypeptides, particularly in prokaryotic host cells, utilizing selected eukaryotic signal sequences. Some of the methods are particularly directed to expression and isolation of antibodies or their fragments (e.g., Fab fragments). The methods are also suitable for expressing other non-antibody polypeptides, particularly in a prokaryotic expression system.

As shown in Examples 6, 7, and 13, using the specific eukaryotic signal peptide sequences (e.g., SEQ ID NO:1 or 2) selected by the present inventors, a number of proteins and polypeptides were efficiently expressed, detected, and/or purified from an *E. coli* host system. These include both antibodies and non-antibody polypeptides.

The invention also provides improved methods for producing and screening polypeptide display libraries. The improvement provides in the display vectors selected eukaryotic signal sequences which allow efficient expression and secretion in prokaryotic systems. Following screening and enrichment of the polypeptide display library, subcloning of polynucleotides encoding the identified polypeptides of interest into an expression vector is greatly facilitated. The operably linked eukaryotic signal sequences enable expression and efficient secretion of the polypeptides of interest in a prokaryotic host system. Efficacy of the improved methods is demonstrated in Examples 8-10.

The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. Although any methods and materials similar or equivalent to those described herein can be used in the practice or testing of the present invention, the preferred methods and materials are described. The following definitions are provided to assist the reader in the practice of the invention.

The basic antibody structural unit is known to comprise a tetramer. Each tetramer is composed of two identical pairs of polypeptide chains, each pair having one "light" (about 25 kDa) and one "heavy" chain (about 50-70 Kda). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J. Mol. Biol.*

196, 901-917 (1987); *Nature* 342, 878-883 (1989); and *J. Mol. Biol.* 186, 651-663 (1989). The term antibody is used to mean whole antibodies and binding fragments thereof. Binding fragments include single chain fragments, Fv fragments and Fab fragments. The term Fab fragment is sometimes used in the art to mean the binding fragment resulting from papain cleavage of an intact antibody. The terms Fab' and F(ab')$_2$ are sometimes used in the art to refer to binding fragments of intact antibodies generated by pepsin cleavage. Here, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. An Fab fragment of the IgG1 subclass contains neither of the two cysteine residues that form the two interchain disulfide bonds between the two heavy chains in the intact immunoglobulin. Usually, Fab fragments are formed by complexing a full-length or substantially full-length light chain with a heavy chain comprising the variable domain and at least the CH1 domain of the constant region. In addition, the C-terminal cysteine on the light chain can be replaced with serine or another amino acid to eliminate the interchain disulfide bond between the heavy and light chains.

Chimeric antibodies are antibodies whose light and heavy chain genes have been constructed, typically by genetic engineering, from immunoglobulin gene segments (e.g., segments encoding the variable region and segments encoding the constant region), for example, belonging to different species. For example, the variable (V) segments of the genes from a mouse monoclonal antibody can be joined to human constant (C) segments, such as IgG1 and IgG4. A typical chimeric antibody is thus a hybrid protein consisting of the V or antigen-binding domain from a mouse antibody and a C or effector domain from a human antibody. Chimeric antibodies have the same or similar binding specificity and affinity as a mouse or other nonhuman antibody that provides the variable regions of the antibody.

The term "human antibody" includes antibodies having variable and constant regions (if present) derived from human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies).

The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An "expression vector" is a polynucleotide construct, generated recombinantly or synthetically, with a series of specified polynucleotide elements that permit transcription of a particular polynucleotide in a host cell. Typically, the expression vector includes a polynucleotide to be transcribed operably linked to a promoter.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods). A target is any molecule for which it is desired to isolate partners with specific binding affinity for the target.

The term "operably linked" refers to a functional relationship between two or more polynucleotide (e.g., DNA) segments. Typically, it refers to the functional relationship of a transcriptional regulatory sequence to a transcribed sequence. For example, a promoter/enhancer sequence of the invention, including any combination of cis-acting transcriptional control elements, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. A polylinker provides a convenient location for inserting coding sequences so the genes are operably linked to a promoter. Polylinkers are polynucleotide sequences that comprise a series of three or more closely spaced restriction endonuclease recognition sequences.

Signal sequence refers to a polynucleotide sequence which encodes a short amino acid sequence (i.e., signal peptide) present at the NH$_2$-terminus of certain proteins that are normally exported by cells to noncytoplasmic locations (e.g., secretion) or to be membrane components. Signal peptides direct the transport of proteins from the cytoplasm to noncytoplasmic locations.

Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

Targets of interest include antibodies, including anti-idiotypic antibodies and autoantibodies present in autoimmune diseases, such as diabetes, multiple sclerosis and rheumatoid arthritis. Other targets of interest are growth factor receptors (e.g., FGFR, PDGFR, EFG, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56, 625-649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. Nos. 5,401,629 and 5,436,128). Other targets are adhesion proteins such as integrins, selectins and immunoglobulin superfamily members (see Springer, *Nature* 346, 425-433 (1990). Osborn, *Cell* 62, 3 (1990); Hynes, *Cell* 69, 11 (1992)). Other targets are cytokines, such as interleukins IL-1 through IL-13, tumor necrosis factors α and β, interferons α, β and γ, tumor growth factor Beta (TGF-β), colony stimulating factor (CSF) and granulocyte monocyte colony stimulating factor (GM-CSF). See *Human Cytokines: Handbook for Basic & Clinical Research* (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241.

Display library members having full-length polypeptide coding sequences have coding sequences the same length as that of the coding sequences originally inserted into a display vector before propagation of the vector.

III. Eukaryotic Signal Sequences for Polypeptide Expression

The present invention provides methods and vectors for expressing in a host cell, particularly a prokaryotic host cell (e.g., E. coli) a protein or a polypeptide of interest, using eukaryotic signal sequences. Preferably, the eukaryotic signal sequence encodes a signal peptide having the sequence of MKILILGIFLFLCSTPAWA (SEQ ID NO:1) or MRTLAIL-AAILLVALQAQA (SEQ ID NO:2). SEQ ID NO:1 corresponds to human ceruloplasmin signal sequence (Accession No. CERU_HUMAN), and SEQ ID NO:2 corresponds to human neutrophil defensin 1,2,3 precursor signal sequence (Accession No. DEFN_HUMAN). Another preferred eukaryotic signal peptide sequence that can be employed in the present invention is MGALAVFAVACLAAVASVAHA (SEQ ID NO:3). It is the signal peptide of Chlamydomonas reinhardtii arylsulfatase precursor (Accession No. ARS_CHLRE). When the protein of interest is an immunoglobulin or a Fab fragment, polynucleotides encoding the Ig heavy chain and light chain are each operably linked to a eukaryotic signal sequence. Such vectors allow expression and secretion of the Ig chains from the host cell and assembly into a functional immunoglobulin molecule or a Fab fragment.

A. Polypeptides of Interest

Various polypeptides of interest can be expressed with the expression vectors of the present invention. In some methods, the polypeptide of interest is an antibody or fragment thereof. The polypeptide to be expressed can be a mouse antibody, a human antibody, or a chimeric antibody. In some preferred embodiments, the polypeptide of interest is a Fab fragment. The antibody to be expressed can be a specific antibody whose heavy and light chain sequences are already known. In other applications, the antibody is identified through screening a polypeptide display library for affinity for a specific target of interest (see, e.g., Examples 4-7). As disclosed in more detail in Section IV, following screening and enrichment, polynucleotide sequences encoding the heavy and light chains of the antibody are transferred from the display vectors to expression vectors. Efficacy of employing eukaryotic signal sequences to express a functional antibody in a prokaryotic system is exemplified in Examples 6-7.

Other than antibodies, various non-antibody polypeptides can also be expressed using the vectors and methods disclosed herein. Exemplified embodiments are provided in Examples 12 and 13. Either eukaryotic or prokaryotic proteins or polypeptides can be expressed in accordance with the methods of the present invention. Preferably, non-antibody polypeptides of interest to be expressed are those which have a native signal peptide. For example, a number of eukaryotic proteins known to have signal sequences (see, e.g., U.S. Pat. No. 5,932,445) can be expressed in prokaryotic host cells using methods of the present invention. These proteins include receptors (nuclear, transmembrane, G protein coupled, and tyrosine kinase), cytokines (chemokines), hormones (growth and differentiation factors), neuropeptides and vasomediators, protein kinases, phosphatases, phospholipases, phosphodiesterases, nucleotide cyclases, matrix molecules (adhesion, cadherin, extracellular matrix molecules, integrin, and selectin), G proteins, ion channels (calcium, chloride, potassium, and sodium), proteases, transporter/pumps (amino acid, protein, sugar, metal and vitamin; calcium, phosphate, potassium, and sodium) and regulatory proteins.

B. Expression Vectors Containing Eukaryotic Signal Sequences

The invention provides expression vectors which comprise at least one transcription unit. The transcription unit comprises a eukaryotic signal sequence operably linked to a polynucleotide encoding the polypeptide of interest. Some of the vectors also comprise a bacterial promoter operably linked to the transcription unit. In some vectors, the bacterial promoter is a rhamnose-inducible promoter. In addition, the expression vectors can also comprise other elements, e.g., origins of replication that is recognized by the host cell, terminator codon, and any other polynucleotide sequences necessary or preferred for appropriate transcription and subsequent translation of the polypeptide in a host cell. The vectors can also contain at least one selectable marker.

In some vectors, polynucleotides encoding multiple copies of the polypeptide of interest are present. The number of copies of the polypeptide of interest can range from 2 to about 100. A preferred number of copies is from about 2 to about 10. In preferred embodiments, the signal sequence peptide is amino terminal to the multiple copies of the polypeptide of interest and these multiple copies are arranged in a continuous uninterrupted manner. In some vectors, polynucleotides encode several different polypeptide of interests can be present. The number of different polypeptide of interests ranging from two to about ten. Preferably, each polypeptide of interest is preceded by a signal sequence peptide (e.g., SEQ ID NOS:1-3) and they are arranged in a continuous, uninterrupted manner with the order in which the polypeptides of interest are arranged being variable. In the above-described polycistronic vectors, multiple polypeptides of interest (either identical in sequence or different) can each be placed under the control of an internal ribosomal entry site (IRES) (Molla A. et al Nature 356: 255-257 (1992); Jang S. K. et al J. of Virol. 263: 1651-1660 (1989)). For example, in some expression vectors of the invention, the different polypeptides of interest can be the heavy and light chains of an immunoglobulin or a Fab fragment of an immunoglobulin. Thus, some of the vectors comprise the bacterial promoter operably linked to a discistronic transcriptional unit which encodes an antibody heavy chain and an antibody light chain that are each operably linked to a eukaryotic signal sequence.

A number of eukaryotic signal sequences can be employed in the expression vectors of the present invention. Tables 3 and 4 provide exemplary signal sequences that can be used in expression and phage display vectors of the present invention. When a dicistronic transcriptional unit is employed to express an immunoglobulin, the signal sequences linked to the heavy chain and the light chain in the vectors can be the same or different, as exemplified in Table 4. In preferred embodiments, the signal peptide encoded by the eukaryotic signal sequence employed is MKILILGIFLFLCSTPAWA (SEQ ID NO:1) or MRTLAILAAILLVALQAQA (SEQ ID NO:2). In some of the preferred embodiments, the light chain is operably linked to a signal sequence (e.g., SEQ ID NO:43) which encodes the peptide sequence as shown in SEQ ID NO:1, and the heavy chain is operably linked to a signal sequence (e.g., SEQ ID NO:45) which encodes the peptide sequence as shown in SEQ ID NO:2. In some other preferred embodiments, both the light and heavy chains are operably linked to a signal sequence (e.g., SEQ ID NOS:43 and 44) which encode the same peptide sequence as shown SEQ ID NO:1.

The eukaryotic signal sequences to be employed in the expression vectors of the present invention can be obtained commercially or synthesized chemically. For example, signal sequences as shown in Tables 3 and 4 can be synthesized according to the solid phase phosphoramidite triester method described, e.g., in Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides can be performed by either native acrylamide gel electrophoresis or by anion-exchange HPLC as described in Pearson & Reanier, *J. Chrom.* 255:137-149 (1983).

Rhamnose-inducible promoters have been characterized in the literature (see, e.g., Egan and Schleif, J. Mol. Biol. 234: 87-98, 1993). Vectors containing a rhamnose-inducible promoter can be readily constructed using the routinely practiced techniques of molecular biology (see generally, Molecular Cloning: A Laboratory Manual (3rd Ed.), Vols. 1-3, Cold Spring Harbor Laboratory, (2001) ("Sambrook"); and Current Protocols In Molecular Biology, Ausubel, ed. John Wiley & Sons, Inc., New York (1997) ("Ausubel")).

In the present invention, the order in which the signal sequence and polynucleotide encoding the polypeptide of interest are arranged within the expression vectors can be varied. In preferred embodiments, the signal sequence is 5' to the polynucleotide encoding the polypeptide of interest. The signal peptide sequence and the polypeptide of interest can be separated by zero to about 1000 amino acids. In preferred embodiments, the signal peptide sequence and the polypeptide of interest are directly adjacent to each other, i.e., separated by zero amino acids.

C. Expression and Secretion in Prokaryotic Host Cells

Preferred host cell for the expression vectors of the present invention is a prokaryotic cell (e.g., *E. coli*). Expression of the polypeptide of interest from the expression vector can be carried in a prokaryotic host cell using methods routinely practiced in the art, e.g., in Sambrook et al., supra, and in Ausubel, supra. Methods for expressing a polynucleotide of interest with the operably linked eukaryotic signal sequence in a prokaryotic host system are also provided in great detail in Section V. When a rhamnose-inducible promoter is employed, the host cell can be either an *E. coli* rhaB+ strain or an *E. coli* rhaB- strain. Induction of expression with rhamnose in these host cells can be performed as described in the Examples below. Expression of polypeptides from a rhamnose inducible promoter has also been described in the art, e.g., Egan and Schleif, supra; Haldimann et al., J. Bacteriol. 177:4121-30, 1998; and Wilms et al., Biotech. and Bioengin. 73:95-103, 2001.

Following expression in the host cell and secretion to the periplasm, the proteins or polypeptides of interest can then be recovered from the culture of host cells. When the polypeptides of interest are immunoglobulin chains, the heavy chain and the light chain are each expressed in the host cell and secreted to the periplasm of the cell. The signal peptides encoded by the eukaryotic signal sequences in the expression vector are then processed from the immunoglobulin chains. The mature heavy and light chains are then assembled to form an intact immunoglobulin or a Fab fragment. Single-chain antibody fragments can be expressed using only one eukaryotic signal sequence.

In some methods, the proteins or polypeptides are first obtained as crude lysate of the host cells. They are then purified by standard protein purification procedures known in the art which may include differential precipitation, molecular sieve chromatography, ion-exchange chromatography, isoelectric focusing, gel electrophoresis, affinity, and immunoaffinity chromatography. These well known and routinely practiced methods are described in, e.g., Sambrook et al., supra; Ausebel, supra., and Wu et al. (eds.), Academic Press Inc., N.Y.; Immunochemical Methods In Cell And Molecular Biology. For example, for purification of recombinantly produced immunoglobulins or Fab fragments, they can be purified with immunoaffinity chromatography by passage through a column containing a resin which has bound thereto target molecules to which the expressed immunoglobulins can specifically bind.

IV. Eukaryotic Signal Sequences in Display Libraries

The present invention provides improved methods of producing and screening a polypeptide display library. The display vectors employed in these methods contain eukaryotic signal sequences (e.g., sequences shown in Tables 3 and 4) that allow efficient secretion in a host system (e.g., a prokaryotic host such as *E. coli*). A polypeptide of interest identified through screening the display library can be subsequently cloned into an expression vector (e.g., a prokaryotic expression vector). The expression vector can then be introduced a host system for production of the identified polypeptide. When an antibody display library is screened, polynucleotides encoding the heavy and/or light chain variable domains are subcloned from the phage display vectors into expression vectors. The expression vectors are introduced into a host and expressed to produce light and heavy chains containing a signal peptide. Mature antibodies are then formed by the heavy and light chains and released from the host.

Methods for constructing and screening an antibody library have been described in U.S. Pat. No. 6,057,098 (which is incorporated herein by reference). Methods for producing and screening phage libraries with display vectors that comprise eukaryotic signal sequences are exemplified in Examples 8-10 below. The antibodies to be displayed and screened can be mouse antibodies or human antibodies. They can also be chimeric antibodies. Polypeptides of particular interest are Fab fragments. The following sections provide detailed guidance for producing and screening polyvalent polypeptide display libraries of the present invention.

A. Replicable Genetic Packages

A replicable genetic package means a cell, spore or virus. The replicable genetic package can be eukaryotic or prokaryotic. A display library is formed by introducing nucleic acids encoding exogenous polypeptides to be displayed into the genome of the replicable genetic package to form a fusion protein with an endogenous protein that is normally expressed from the outersurface of the replicable genetic package. Expression of the fusion protein, transport to the outersurface and assembly results in display of exogenous polypeptides from the outersurface of the genetic package.

The genetic packages most frequently used for display libraries are bacteriophage, particularly filamentous phage, and especially phage M13, Fd and F1. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wildtype copies of coat protein expressed from the helper phage. See, e.g., Garrard, WO 92/09690.

Eukaryotic viruses can be used to display polypeptides in an analogous manner. For example, display of human heregulin fused to gp70 of Moloney murine leukemia virus has been reported by Han et al., *Proc. Natl. Acad. Sci. U.S.A* 92, 9747-9751 (1995). Spores can also be used as replicable genetic packages. In this case, polypeptides are displayed from the outersurface of the spore. For example, spores from *B. subtilis* have been reported to be suitable. Sequences of coat proteins of these spores are provided by Donovan et al., *J. Mol. Biol.* 196, 1-10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outersurface proteins are discussed by Ladner et al., U.S. Pat. No. 5,571,698, and Georgiou et al., *Nature Biotechnology* 15, 29-34 (1997) and references cited therein. For example, the lamB protein of *E. coli* is suitable.

B. Library Display of Antibodies

Multivalent phage display of antibody libraries can be produced as described in U.S. Pat. No. 6,057,098. Briefly, the starting material is a library of phage in which a library member comprises a phage capable of displaying from its outer surface a fusion protein comprising a phage coat protein, an antibody light or heavy chain variable domain, and a tag. In at least some members, the antibody heavy or light chain is complexed with a partner antibody heavy or light chain variable domain chain, the complex forming a Fab fragment to be screened. The fusion protein and/or the partner antibody heavy or light chain are encoded by segment(s) of the genome of the phage. In addition, the display vector contains at least one eukaryotic signal sequence operably linked to antibody heavy or light chain (e.g., as shown in Tables 3 and 4). When display of a Fab fragment is intended, the display vector contains a first eukaryotic signal sequence operably linked to the heavy chain sequence and a second eukaryotic signal sequence operably linked to the light chain sequence. The first and second signal sequences can be the same or different. In some methods, the signal sequence encodes a signal peptide sequence as shown in SEQ ID NO:1, 2, or 3. For example, the signal sequence linked to the light chain can be SEQ ID NO:43 which encodes the signal peptide sequence as shown in SEQ ID NO:1, and the signal sequence linked to the heavy chain can be SEQ ID NO:45 which encodes the signal peptide shown in SEQ ID NO:2 (as exemplified in Example 8). Alternatively, both chains can be operably linked to signal sequences, e.g., SEQ ID NO:43 and 44, which encode the same signal peptide sequence shown in SEQ ID NO:1.

The number of copies of the fusion protein and the partner antibody chain displayed per phage vary between library members. The library or a fraction thereof is contacted with a receptor having a specific affinity for the tag under conditions whereby library members displaying at least two copies of the fusion protein are preferentially bound to immobilized receptor by multivalent bonds between the receptor and the at least two copies of the tag. Library members bound to the receptor are then separated from unbound library members to produce an sublibrary enriched relative to the library for members displaying at least two copies of the fusion protein.

1. Single or Double Chain Antibody Libraries

Antibody libraries can be single or double chain. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner et al., WO 88/06630; McCafferty et al., WO 92/01047. Double-chain antibodies are formed by noncovalent or covalent association of heavy and light chains or binding fragments thereof. Double-chain antibodies can also be formed from two single-chain antibodies that form a stable dimer comprising two antibody binding sites (see Schier et al., *J. Mol. Biol.* 255, 28-43 (1996); Arndt et al., *Biochemistry* 37, 12918-12926 (1998). The diversity of antibody libraries can arise from obtaining antibody-encoding sequences from a natural source, such as a nonclonal population of immunized or unimmunized B cells. Alternatively, or additionally, diversity can be introduced by artificial mutagenesis as discussed for other proteins.

Nucleic acids encoding polypeptides to be displayed optionally flanked by spacers are inserted into the genome of a replicable genetic package as discussed above by standard recombinant DNA techniques (see generally, Sambrook et al., Molecular Cloning A Laboratory Manual, 3rd Ed., 2000, Cold Spring Harbor Laboratory Press, incorporated by reference herein). The nucleic acids are ultimately expressed as polypeptides (with or without spacer or framework residues) fused to all or part of the an outersurface protein of the replicable package. Libraries often have sizes of about $10^3$, $10^4$, $10^6$, $10^7$, $10^8$ or more members.

Double-chain antibody display libraries can be produced as described in, e.g., Dower, U.S. Pat. No. 5,427,908; Huse WO 92/06204; Huse, in Antibody Engineering, (Freeman 1992), Ch. 5; Kang, WO 92/18619; Winter, WO 92/20791; McCafferty, WO 92/01047; Hoogenboom WO 93/06213; Winter et al., *Annu. Rev. Immunol.* 12, 433-455 (1994); Hoogenboom et al., *Immunological Reviews* 130, 41-68 (1992); Soderlind et al., *Immunological Reviews* 130, 109-124 (1992). In a preferred embodiment, one antibody chain is fused to a phage coat protein, as is the case in single chain libraries. The partner antibody chain is complexed with the first antibody chain, but the partner is not directly linked to a phage coat protein. Either the heavy or light chain can be the chain fused to the coat protein. Whichever chain is not fused to the coat protein is the partner chain. This arrangement is typically achieved by incorporating nucleic acid segments encoding one antibody chain gene into either gIII or gVIII of a phage display vector to form a fusion protein comprising a signal sequence, an antibody chain, and a phage coat protein. Nucleic acid segments encoding the partner antibody chain can be inserted into the same vector as those encoding the first antibody chain. Optionally, heavy and light chains can be inserted into the same display vector linked to the same promoter and transcribed as a polycistronic message, e.g., a dicistronic mRNA encoding a Fab fragment and the operably linked signal peptides.

Alternatively, nucleic acids encoding the partner antibody chain can be inserted into a separate vector (which may or may not be a phage vector). In this case, the two vectors are expressed in the same cell (see WO 92/20791). The sequences encoding the partner chain are inserted such that the partner chain is linked to a signal sequence, but is not fused to a phage coat protein. Both antibody chains are expressed and exported to the periplasm of the cell where they assemble and are incorporated into phage particles.

Antibody encoding sequences can be obtained from lymphatic cells of a human or nonhuman animal. Often the cells have been immunized, in which case immunization can be performed in vivo before harvesting cells, or in vitro after harvesting cells, or both. Spleen cells of an immunized animal are a preferred source material. Immunization of humans is only possible with certain antigens. The number of different H chain genes and L chain genes in a spleen from an immunized animal is about $10^6$, which can be assembled in $10^{12}$ potential combinations.

Rearranged immunoglobulin genes can be cloned from genomic DNA or mRNA. For the latter, mRNA is extracted from the cells and cDNA is prepared using reverse transcriptase and poly-dT oligonucleotide primers. Primers for cloning antibody encoding sequences are discussed by Larick et al., Bio/Technology 7, 934 (1989), Danielsson & Borrebaceick, in Antibody Engineering. A Practical Guide (Freeman, NY, 1992), page 89 and Huse, id. at Ch. 5.

Repertoires of antibody fragments have been constructed by combining amplified VH and VL sequences together in several ways. Light and heavy chains can be inserted into different vectors and the vectors combined in vitro (Hogrefe et al., Gene 128, 119-126 (1993)) or in vivo (Waterhouse et al., Nucl. Acids. Res. 21, 2265-66 (1993)). Alternatively, the light and heavy chains can be cloned sequentially into the same vector (Barbas et al., Proc. Natl. Acad. Sci. U.S.A 88, 7987-82 (1991)) or assembled together by PCR and then inserted into a vector (Clackson et al., Nature 352, 624-28 (1991)). Repertoires of heavy chains can be also be combined with a single light chain or vice versa. Hoogenboom et al., J. Mol. Biol. 227, 381-88 (1992).

Some exemplary vectors and procedures for cloning populations of heavy chain and light chain encoding sequences have been described by Huse, WO 92/06204. Diverse populations of sequences encoding Hc polypeptides are cloned into M13IX30 and sequences encoding Lc polypeptides are cloned into M13IX11. The populations are inserted between the XhoI-SeeI or StuI restriction enzyme sites in M13IX30 and between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the Hc and Lc encoding sequences and their associated vector sequences. The two pairs are symmetrically orientated about the cloning site so that only the vector proteins containing the sequences to be expressed are exactly combined into a single vector.

2. Chimeric or Human Antibody Libraries

The improved methods for producing and screening multivalent display libraries of the present invention encompass chimeric or human antibody libraries. A chimeric antibody comprises at least one chimeric antibody chain, including, for example, that the antibody has a variable region from a first species, and a constant region from a second species. Some chimeric antibodies, such as Fab fragments, have a chimeric heavy chain and a chimeric light chain. Some chimeric light chains comprise a light chain variable region from a first species, and a constant region from a second species. Likewise some chimeric heavy chains comprise a heavy chain variable region from a first species, and a heavy chain constant region from a second species. An intact antibody can comprise two copies of a chimeric light chain and two copies of a chimeric heavy chain. A chimeric Fab fragment can comprise a chimeric light chain and a chimeric heavy chain. For chimeric antibodies that comprise a variable region from a first species and a constant region from a second species, the variable regions are typically obtained from a nonhuman species, such as mouse, rat, rabbit, guinea pig, cow, horse, sheep, vulcher, monkey or chimpanzee. The constant regions are typically human for chimerics intended for use in humans or from the animal species of intended use for veterinary applications. In a Fab fragment, the heavy chain constant region usually comprises a CH1 region, and the light chain constant region is an intact light chain constant region, such as C-kappa or C-lambda. In an intact IgG antibody, the heavy chain constant region typically includes CH1, hinge, CH2, and CH3 regions, and the light chain is an intact C-kappa or C-lambda light chain.

Libraries of polyclonal chimeric antibodies of the present invention can be produced accordingly to the methods described in, e.g., U.S. patent application Ser. No. 09/410,903, filed Oct. 2, 1999 issued as U.S. Pat. No. 6,420,113 (which is incorporated herein by reference). In some methods, the phage vector or other replicable genetic package contains a first eukaryotic signal sequence operably linked to the heavy variable region and a second eukaryotic signal sequence operably linked to the light chain variable region. In addition, a heavy chain constant region (the CH1 region) and the light chain constant region are inserted respectively in frame with the heavy and light chain variable region. Examples of eukaryotic signal sequences suitable for the display vectors are provided in Tables 3 and 4.

In some methods, the replicable genetic packages or phage display libraries are capable of expressing and displaying chimeric Fab fragments comprising nonhuman variable regions and human constant regions. For example, the display vector can encode a human CH1 region in frame with an inserted heavy chain variable region and an intact human light chain region, such as kappa or lambda, in frame with an inserted light chain variable region. In some methods, the expression vector is designed to encode an additional segment of the human heavy chain constant region (typically, hinge, CH2 and CH3) regions in-frame with the segment of the chimeric heavy chain present in the Fab fragment. The resulting population of modified vectors expresses a population of intact antibodies.

The invention also provides methods for displaying and screening phage libraries of human antibodies which contain eukaryotic signal sequences. The human antibodies are originally expressed in nonhuman transgenic animals to produce populations of human antibodies having unexpected characteristics. These characteristics include unusually high binding affinities (e.g., pM dissociation constants in some instances), virtually unlimited numbers of such antibodies, and a high degree of enrichment for such antibodies in the population. Libraries of human antibodies with such characteristics can be produced as described in, e.g., U.S. patent application Ser. No. 09/453,234, filed Dec. 1, 1999 (which is incorporated herein by reference) and WO 01/25492. Briefly, the methods entail immunizing a nonhuman transgenic animal having human immunoglobulin genes (e.g., transgenic mice). The animal expresses a diverse range of human antibodies that bind to the antigen. Nucleic acids encoding the antibody chain components of such antibodies are then cloned from the animal into a display vector. Typically, separate populations of nucleic acids encoding heavy and light chain sequences are cloned, and the separate populations then recombined on insertion into the vector, such that any given copy of the vector receives a random combination of a heavy and light chains.

C. Enrichment for Polyvalent Display Members

Members of a library displaying multiple copies of a polypeptide are comparatively rare in display libraries. To enrich for library members displaying more than one polypeptide before the library is contacted with a screening target, paired tags and receptors can be employed. A tag may be anything that is bound by a receptor but is typically a short peptide sequence and a receptor is any agent that shows specific but reversible binding for the tag and can be immobilized to a support. Various tag-receptor combinations suitable for the present invention have been disclosed in U.S. Pat. No. 6,057,098. For example, epitope and antibody pair include hexapeptide ligands which are known to have high affinity for the anti-dynorphin mAb 32.39 (see Barrett et al., *Neuropeptides* 6, 113-120 (1985) and Cull et al., *PNAS* 89, 1865-1869 (1992)), and a variety of short peptides are known to bind the MAb 3E7 (Schatz, *Biotechnology* 11, 1138-43 (1993)). Another combination of tag and antibody is described by Blanar & Rutter, *Science* 256, 1014-1018 (1992). Still another example of a tag-receptor pair is the FLAG™ system (Kodak).

Receptors are often labeled with biotin allowing the receptors to be immobilized to an avidin-coated support. Biotin labeling can be performed using the biotinylating enzyme, BirA (see, e.g., Schatz, *Biotechnology* 11, 1138-43 (1993)).

A nucleic acid sequence encoding a tag is inserted into a display vector in such a manner that the tag is expressed as part of the fusion protein containing the polypeptide to be displayed and an outersurface protein of the replicable genetic package. The relative ordering of these components is not critical provided that the tag and polypeptide to be displayed are both exposed on the outersurface of the package. For example, the tag can be placed between the outersurface protein and the displayed polypeptide or at or near the exposed end of the fusion protein. The tag can be part of the displayed polypeptide common to all library members such as the constant domain of an antibody.

In replicable genetic packages displaying Fab fragments, a tag can be fused to either the heavy or the light Fab chain, irrespective which chain is linked to a phage coat protein. Optionally, two different tags can used one fused to each of the heavy and light chains. One tag is usually positioned between the phage coat protein and antibody chain linked thereto, and the other tag is positioned at either the N- or C-terminus of the partner chain.

D. Selection of Polyvalent Members

Selection of polyvalent library members is performed by contacting the library with the receptor for the tag component of library members. Usually, the library is contacted with the receptor immobilized to a solid phase and binding of library members through their tag to the receptor is allowed to reach equilibrium. The complexed receptor and library members are then brought out of solution by addition of a solid phase to which the receptor bears affinity (e.g., an avidin-labeled solid phase can be used to immobilize biotin-labeled receptors). Alternatively, the library can be contacted with receptor in solution and the receptor subsequently immobilized. The concentration of receptor should usually be at or above the Kd of the tag/receptor during solution phase binding so that most displayed tags bind to a receptor at equilibrium. When the receptor-library members are contacted with the solid phase only the library members linked to receptor through at least two displayed tags remain bound to the solid phase following separation of the solid phase from library members in solution. Library members linked to receptor through a single tag are presumably sheared from the solid phase during separation and washing of the solid phase. After removal of unbound library members, bound library members can be dissociated from the receptor and solid phase by a change in ionic strength or pH, or addition of a substance that competes with the tag for binding to the receptor. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The average number of polypeptides per library member selected by this method is affected by a number of factors. Decreasing the concentration of receptor during solution-phase binding has the effect of increasing the average number of polypeptides in selected library members. An increase in the stringency of the washing conditions also increases the average number of polypeptides per selected library member. The physical relationship between library members and the solid phase can also be manipulated to increase the average number of polypeptides per library member. For example, if discrete particles are used as the solid phase, decreasing the size of the particles increases the steric constraints of binding and should require a higher density of polypeptides displayed per library member.

For Fab libraries having two tags, one linked to each antibody chain, two similar rounds of selection can be performed, with the products of one round becoming the starting materials for the second round. The first round of selection is performed with a receptor to the first tag, and the second round with a receptor to the second tag. Selecting for both tags enriches for library members displaying two copies of both heavy and light antibody chains (i.e., two Fab fragments).

E. Selection for Affinity to Target of Interest

Library members enriched for polyvalent display of Fab or other polypeptides are screened for binding to a target of interest. The target of interest can be any molecule of interest for which it is desired to identify binding partners. The target should lack specific binding affinity for the tag(s), because in this step it is the displayed polypeptides being screened, and not the tags that bind to the target. The screening procedure at this step is closely analogous to that in the previous step except that the affinity reagent is a target of interest rather than a receptor to a tag. The enriched library members are contacted with the target which is usually labeled (e.g., with biotin) in such a manner that allows its immobilization. Binding is allowed to proceed to equilibrium and then target is brought out of solution by contacting with the solid phase in a process known as panning (Parmley & Smith, *Gene* 73, 305-318 (1988)). Library members that remain bound to the solid phase throughout the selection process do so by virtue of polyvalent bonds between them and immobilized target molecules. Unbound library members are washed away from the solid phase.

Usually, library members are subject to amplification before performing a subsequent round of screening. Often, bound library members can be amplified without dissociating them from the support. For example, gene VIII phage library members immobilized to beads, can be amplified by immersing the beads in a culture of *E. coli*. Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members are now enriched for two features: multivalent display of polypeptides and display of polypeptides having specific affinity for the target of interest. However, after subsequent amplification, to produce a secondary library, the secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been performed.

In a variation, affinity screening to a target is performed in competition with a compound that resembles but is not identical to the target. Such screening preferentially selects for library members that bind to a target epitope not present on the compound. In a further variation, bound library members can be dissociated from the solid phase in competition with a compound having known crossreactivity with a target for an antigen. Library members having the same or similar binding specificity as the known compound relative to the target are preferentially eluted. Library members with affinity for the target through an epitope distinct from that recognized by the compound remain bound to the solid phase.

Discrimination in selecting between polypeptides of different monovalent affinities for the target is affected by the valency of library members and the concentration of target during the solution phase binding. Assuming a minimum of i labeled target molecules must be bound to a library member to immobilize it on a solid phase, then the probability of immobilization can be calculated for a library member displaying n polypeptides. From the law of mass action, the bound/free polypeptide fraction, F, is K[targ]/(1+K[targ]), where [targ] is the total target concentration in solution. Thus, the probability that i or more displayed polypeptides per library member are bound by the labeled target ligand is given by the binomial probability distribution:

$$\sum_{y=i}^{n} (n!/[y!(n-y)!]F^y(1-F)^{n-y}$$

As the probability is a function of K and [target], multivalent display members each having a monovalent affinity, K, for the target can be selected by varying the concentration of target. The probabilities of solid-phase immobilization for i=1, 2, or 3, with library members exhibiting monovalent affinities of 0.1/[Ag], 1/[Ag], and 10/[Ag], and displaying n polypeptides per member are:

| n | K = 0.1/[targ] | K = 1/[targ] | K = 10/[targ] |
|---|---|---|---|
| Probability of Immobilization (i = 1) | | | |
| 1 | 0.09 | 0.5 | 0.91 |
| 2 | 0.17 | 0.75 | 0.99 |
| 3 | 0.25 | 0.875 | |
| 4 | 0.32 | 0.94 | |
| 5 | 0.38 | 0.97 | |
| 6 | 0.44 | 0.98 | |
| 7 | 0.49 | 0.99 | |
| 8 | 0.53 | | |
| 9 | 0.58 | | |
| 10 | 0.61 | | |
| 20 | 0.85 | | |
| 50 | 0.99 | | |
| Probability of Immobilization (i = 2) | | | |
| 2 | 0.008 | 0.25 | 0.83 |
| 3 | 0.023 | 0.50 | 0.977 |
| 4 | 0.043 | 0.69 | 0.997 |
| 5 | 0.069 | 0.81 | |
| 6 | 0.097 | 0.89 | |
| 7 | 0.128 | 0.94 | |
| 8 | 0.160 | 0.965 | |
| 9 | 0.194 | 0.98 | |
| 20 | 0.55 | | |
| 50 | 0.95 | | |
| Probability of Immobilization (i = 3) | | | |
| 3 | 0.00075 | 0.125 | 0.75 |
| 4 | 0.0028 | 0.31 | 0.96 |
| 5 | 0.0065 | 0.50 | 0.99 |
| 6 | 0.012 | 0.66 | |
| 7 | 0.02 | 0.77 | |
| 8 | 0.03 | 0.855 | |
| 9 | 0.0415 | 0.91 | |
| 10 | 0.055 | 0.945 | |
| 12 | 0.089 | 0.98 | |
| 14 | 0.128 | 0.99 | |
| 20 | 0.27 | | |
| 50 | 0.84 | | |

The above tables show that the discrimination between immobilizing polypeptides of different monovalent binding affinities is affected by the valency of library members (n) and by the concentration of target for the solution binding phase. Discrimination is maximized when n (number of polypeptides displayed per phage) is equal to i (minimum valency required for solid phase binding). Discrimination is also increased by lowering the concentration of target during the solution phase binding. Usually, the target concentration is around the Kd of the polypeptides sought to be isolated. Target concentrations of $10^{-8}$-$10^{-10}$ M are typical.

Enriched libraries produced by the above methods are characterized by a high proportion of members encoding polypeptides having specific affinity for the target. For example, at least 10, 25, 50, 75, 95, or 99% of members encode polypeptides having specific affinity for the target. The exact percentage of members having affinity for the target depends whether the library has been amplified following selection, because amplification increases the representation of genetic deletions. However, among members with full-length polypeptide coding sequences, the proportion encoding polypeptides with specific affinity for the target is very high (e.g., at least 50, 75, 95 or 99%). Not all of the library members that encode a polypeptide with specific affinity for the target necessarily display the polypeptide. For example, in a library in which 95% of members with full-length coding sequences encode polypeptides with specific affinity for the target, usually fewer than half actually display the polypeptide. Usually, such libraries have at least 4, 10, 20, 50, 100, 1000, 10,000 or 100,000 different coding sequences. Usually, the representation of any one such coding sequences is no more than 50%, 25% or 10% of the total coding sequences in the library.

V. Subcloning and Expression in Host System

A. Subcloning

Screening of display library members typically results in a subpopulation of library members having specific affinity for a target. In some methods, clonal isolates of library members are obtained, and these isolates are used directly in various other analyses. In other methods, clonal isolates of library member are obtained, and polynucleotide sequences encoding antibody chains are amplified from each isolate. Typically, heavy and light chains are amplified as components of the same polynucleotide molecule before transfer to an expression vector, such that combinations of heavy and light chain existing in the display vector are preserved in the expression vector. In addition, each of the signal sequences is also transferred to the expression vector in which its operable linkage to the antibody chain is preserved. The expression vector can be a prokaryotic vector as disclosed above. The expression vector can also be an eukaryotic vector. Further, in some methods, the polynucleotides of interest (e.g., a Fab-encoding sequences) in one expression vector (e.g., the prokaryotic expression vectors discussed in Section III) are transferred into another expression vectors (other prokaryotic vectors or eukaryotic vectors).

For displayed antibody chains that include both human variable regions and human constant regions, typically nucleic acids encoding both the variable region and constant region are subcloned. In other methods, nucleic acids encoding antibody chains are amplified and subcloned en masse from a pool of library members into multiple copies of an expression vector without clonal isolation of individual members. The subcloning process, as described in detail below, is essentially the same for transfer of a mixed population of polynucleotides from a display vector to an expression vector as that for transferring nucleic acids obtained from a clonal isolate of an individual display vector.

Polynucleotides encoding antibody chains to be subcloned can be excised by restriction digestion of flanking sequences or can be amplified by PCR using primers to sites flanking the coding sequences. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila, et al., *Nucleic Acids Res.* 19:967 (1991); Eckert, et al., *PCR Methods and Applications* 1:17 (1991); PCR (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. For Fab libraries, if heavy and light chains are inserted adjacent or proximate to each other in a display vector, the two chains can be amplified or excised together. For some Fab libraries, only the variable domains of antibody chain(s) are excised or amplified. If the heavy or light chains of a Fab library are excised or amplified separately, they can subsequently be inserted into the same or different expression vectors.

When eukaryotic expression vectors are used, the heavy chain and light chain sequences can be transferred into two separate vectors. On the other hand, the heavy chain and light chain sequences can be subcloned into the same expression vector. In the latter case, the light chain and heavy chain can be put under the control of two separate eukaryotic promoters. Alternatively, the heavy and light chain sequences can be put under the control of one promoter in the same vector. However, to ensure ribosome binding to the downstream sequence (e.g., the light chain sequence), an IRES sequence can be inserted in operative association with the downstream sequence.

Having excised or amplified fragments encoding displayed antibody chains, the fragments are usually size-purified on an agarose gel or sucrose gradient. Typically, the fragments run as a single sharp full-length band with a smear at lower molecular corresponding to various deleted forms of coding sequence. The band corresponding to full-length coding sequences is removed from the gel or gradient and these sequences are used in subsequent steps.

The next step is to join the nucleic acids encoding full-length coding sequences to an expression vector thereby creating a population of modified forms of the expression vector bearing different inserts. This can be done by conventional ligation of cleaved expression vector with a mixture of inserts cleaved to have compatible ends. Alternatively, the use of restriction enzymes on insert DNA can be avoided. This method of cloning is beneficial because naturally encoded restriction enzyme sites may be present within insert sequences, thus, causing destruction of the sequence when treated with a restriction enzyme. For cloning without restricting, a mixed population of inserts and linearized vector sequences are treated briefly with a 3' to 5' exonuclease such as T4 DNA polymerase or exonuclease III. See Sambrook, et al., Molecular Cloning, A Laboratory Manual (2nd Ed., CSHP, New York 1989). The protruding 5' termini of the insert generated by digestion are complementary to single-stranded overhangs generated by digestion of the vector. The overhangs are annealed, and the re-annealed vector transfected into recipient host cells. The same result can be accomplished using 5' to 3' exonucleases rather than a 3' to 5' exonuclease.

Preferably, ligation of inserts to expression vector is performed under conditions that allow selection against re-annealed vector and uncut vector. A number of vectors containing conditional lethal genes that allow selection against re-annealed vector under nonpermissive conditions are known. See, e.g., Conley & Saunders, *Mol. Gen. Genet.* 194: 211-218 (1984). These vectors effectively allow positive selection for vectors having received inserts. Selection can also be accomplished by cleaving an expression vector in such a way that a portion of a positive selection marker (e.g., antibiotic resistance) is deleted. The missing portion is then supplied by full-length inserts. The portion can be introduced at the 3' end of polypeptide coding sequences in the display vector, or can be included in a primer used for amplification of the insert.

The choice of expression vector depends on the intended host cells in which the vector is to be expressed. Typically, the vector includes a promoter and other regulatory sequences in operable linkage to the inserted coding sequences that ensure the expression of the latter. Use of an inducible promoter is advantageous to prevent expression of inserted sequences except under inducing conditions. Inducible promoters include arabinose, lacZ, metallothionein promoter or a heat shock promoter. Cultures of transformed organisms can be expanded under noninducing conditions without biasing the population for coding sequences whose expression products are better tolerated by the host cells. The vector may also provide a secretion signal sequence positioned to form a fusion protein with polypeptides encoded by inserted sequences, although often inserted polypeptides are linked to a signal sequences before inclusion in the vector. Vectors to be used to receive sequences encoding antibody light and heavy chain variable domains sometimes encode constant regions or parts thereof that can be expressed as fusion proteins with inserted chains thereby leading to production of intact antibodies or fragments thereof. Typically, such constant regions are human. Conservative mutations although not preferred can be tolerated. For example, if display packages display a heavy chain variable region linked to a $C_H1$ constant region and a light chain variable region linked to an intact light chain constant region, and the complete antibody chains are transferred from the display vector to the expression vector, then the expression vector can be designed to encode human heavy chain constant region hinge, $C_H2$ and $C_H3$ regions in-frame with the $C_H1$ region of the inserted heavy chain nucleic acid thereby resulting in expression of an intact antibody. Of course, many minor variations are possible as to precisely which segment of the human heavy chain constant region is supplied by the display package and which by the expression vector. For example, the display package can be designed to include a $C_H1$ region, and some or all of the hinge region. In this case, the expression vector is designed to supply the residual portion of the hinge region (if any) and the $C_H2$ and $C_H3$ regions for expression of intact antibodies.

B. Host Systems And Expression Various host systems can be used for expressing the polynucleotides of interest as discussed in Sections III and IV. As discussed in Section III, *E. coli* is one prokaryotic host useful particularly for cloning the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda or phage T7. The promoters typically control expression, optionally with an operator sequence, and have ribosome binding site sequences and the like, for initiating and completing transcription and translation.

Other microbes, such as yeast, can also be used for expression. *Saccharomyces* is a preferred host, with suitable vectors having expression control sequences, such as promoters, including 3-phosphoglycerate kinase or other glycolytic enzymes or galactose promoters, and an origin of replication, termination sequences and the like as desired. Insect cells in combination with baculovirus vectors can also be used.

Mammalian tissue cell culture can also be employed to express and produce the polypeptides of interest of the present invention (see Winnacker, From Genes to Clones (VCH Publishers, N.Y., N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include expression control sequences, such as an origin of replication, a promoter, and an enhancer (Queen, et al., *Immunol. Rev.* 89:49-68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra).

Once expressed, collections of antibodies are purified from culture media and host cells. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like (see generally Scopes, Protein Purification (Springer-Verlag, N.Y., 1982)).

The above methods result in novel libraries of nucleic acid sequences encoding antibody chains having specific affinity for a chosen target. The libraries of nucleic acids typically have at least 5, 10, 20, 50, 100, 1000, $10^4$ or $10^5$ different members. Usually, no single member constitutes more than 25 or 50% of the total sequences in the library. Typically, at least 25, 50%, 75, 90, 95, 99 or 99.9% of library members encode antibody chains with specific affinity for the target molecules. The nucleic acid libraries can exist in free form, as components of any vector or transfected as a component of a vector into host cells. In some libraries, at least 90, 95 or 99% of nucleic acids encoding antibody heavy chains encode heavy chains of IgG isotype. In some libraries, the nucleic acids encoding heavy chains of members having specific affinity for the target have a median of at least 5, 10, 14, 15, 20 or 25 somatic nucleotide mutations per chain. In some libraries, the nucleic acids encoding light chains of members having specific affinity for the target have a median of a least 2, 3, 5, 10, 15, 20 or 25 somatic nucleotide mutations per chain.

The nucleic acid libraries can be expressed to generate polyclonal libraries of antibodies having specific affinity for a target. The composition of such libraries is determined from the composition of the nucleotide libraries. Thus, such libraries typically have at least 5, 10, 20, 50, 100, 1000, $10^4$ or $10^5$ members with different amino acid composition. Usually, no single member constitutes more than 25 or 50% of the total polypeptides in the library. The percentage of antibody chains in an antibody chain library having specific affinity for a target is typically lower than the percentage of corresponding nucleic acids encoding the antibody chains. The difference is due to the fact that not all polypeptides fold into a structure appropriate for binding despite having the appropriate primary amino acid sequence to support appropriate folding. In some libraries, at least 25, 50, 75, 90, 95, 99 or 99.9% of antibody chains have specific affinity for the target molecules. Again, in libraries of multi-chain antibodies, each antibody (such as a Fab or intact antibody) is considered a library member. In some libraries, at least 90, 95 or 99% of heavy chains are of IgG isotype. In some libraries, the heavy chains having specific affinity for the target have a median of at least 1, 2, 3, 4, 5, 7, 10, 12, 15, or 20 somatic amino acid mutations per chain. In some libraries, the light chains having specific affinity for the target have a median of a least of 1, 2, 3, 5, 10, 12, 15, 20 somatic amino acid mutations per chain. The different antibody chains differ from each other in terms of fine binding specificity and affinity for the target. Some such libraries comprise members binding to different epitopes on the same antigen. Some such libraries comprises at least two members that bind to the same antigen without competing with each other.

Polyclonal libraries of human antibodies resulting from the above methods are distinguished from natural populations of human antibodies both by the high percentages of high affinity binders in the present libraries, and in that the present libraries typically do not show the same diversity of antibodies present in natural populations. The reduced diversity in the present libraries is due to the nonhuman transgenic animals that provide the source materials not including all human immunoglobulin genes. For example, some polyclonal antibody libraries are free of antibodies having lambda light chains. Some polyclonal antibody libraries of the invention have antibody heavy chains encoded by fewer than 10, 20, 30 or 40 $V_H$ genes. Some polyclonal antibody libraries of the invention have antibody light chains encoded by fewer than 10, 20, 30 or 40 $V_L$ genes.

Although the foregoing invention has been described in detail for purposes of clarity of understanding, it will be obvious that certain modifications may be practiced within the scope of the appended claims. All publications and patent documents cited in the present application are hereby incorporated by reference in their entirety for all purposes to the same extent as if each were so individually denoted. The following examples are provided for illustrative purposes and are not intended to limit the scope of the invention.

EXAMPLES

Example 1

Construction of Expression Vectors

Expression vectors were constructed having polynucleotides encoding polypeptides to be expressed along with promoters operably linked to the polynucleotides, including lac and rhamnose promoters as described herein.

Preparation of AL1.3 Expression Vector

An expression vector similar to those described in Example 17 of U.S. Pat. No. 6,057,098 was developed for cloning Fabs with different signal sequences on the kappa chain. The vector is a modified pBR322 plasmid, designated AL1.3, that contains a lac promoter (Plac), ampicillin resistance gene, NsiI and HindIII restriction sites, and a partial tetracycline resistance gene.

Polymerase chain reaction (PCR) primers, B and C (Table 2), were made corresponding to the sequence at the 3' and 5' ends of the lac promoter, respectively. The primers B and C, in addition to having sequence specific to Plac, contain approximately 20 nucleotides of pBR vector sequence at their 5'-ends complementary to the 3' side of the HindIII restriction site and the 5' side of the EcoRI restriction site, respectively. In addition, primer B places a NsiI restriction site at the 3'-end of the lac promoter for the purpose of linearizing the final construct in preparation for introducing the antibody cassettes. Five PCR reactions were performed, each containing 100 pmol of primer B, 100 pmol of primer C, 2 units of Expand polymerase (Roche Applied Science, Indianapolis, Ind.), 10 µp 2 mM deoxynucleotide triphosphates (dNTPs, Roche Applied Science, Indianapolis, Ind.), 10 µp 10x Expand reaction buffer, 50 ng BS51 uracil template (Example 8), and water to 100 µl. The reactions were carried out in a Perkin-Elmer thermal cycler (Model 9600, Perkin-Elmer, Emoryville, Calif.) using the following thermal profile: one cycle of denaturation at 94° C. (1 minute); ten cycles of denaturation (15 sec, 94° C.), annealing (30 sec, 55° C.), elongation (60 sec, 72° C.); twenty cycles of denaturation (15 sec, 94° C.), annealing (30 sec, 55° C.), elongation (80 sec plus 20 sec for each additional cycle, 72° C.); elongation (6 min, 72° C.); soak (4° C., forever). The Plac PCR product was verified by agarose gel electrophoresis. The PCR product was fractionated by agarose gel electrophoresis and full-length product excised from the gel, and purified with a QiaQuick column (Qiagen, Valencia, Calif.) as per manufacturers' recommendations. The concentration of the insert was determined by $A_{260}$ purified, and resuspended in water.

An expression vector similar to those described in Example 17 of U.S. Pat. No. 6,057,098 was altered to receive the Plac insert by digesting the vector with EcoRI and HindIII (Roche Applied Sciences, Indianapolis, Ind.) following manufacturers' recommendations. Digestion of the expression vector with these enzymes produces an identical pBR322 backbone as would be obtained by digesting pBR322 vector. The digested vector was run on agarose gel electrophoresis and the product corresponding to the pBR322 backbone was excised from the gel and purified using QiaQuick columns (Qiagen, Valencia, Calif.) following manufacturers' recommendations. The concentration of the insert was determined by $A_{260}$.

The Plac insert and EcoRI/HindIII linearized pBR322 vector were prepared for T4 exonuclease digestion by adding 1.0 µl of 10x Buffer A (Roche Applied Sciences, Indianapolis, Ind.) to 1.0 µg of DNA and bringing the final volume to 9 µl with water. The samples were digested for 4 minutes at 30° C. with 1 µl (1U/µl) of T4 DNA polymerase (Roche Applied Sciences, Indianapolis, Ind.). The T4 DNA polymerase was heat inactivated by incubation at 70° C. for 10 minutes. The samples were cooled, briefly spun. In a separate tube, 12 ng of the digested Plac insert, 100 ng of digested vector, and 1.0 µl of 10x annealing buffer (200 mM Tris pH 7.0, 20 mM $MgCl_2$, 500 mM NaCl) were added and the volume brought to 10 µl with water. The sample was then heated to 70° C. for 2 minutes and cooled over 20 minutes to 30° C. to allow the complementary 5' single-stranded overhangs of the insert and vector resulting from the exonuclease digestion to anneal together. The insert and vector were ligated together by adding 1.3 µl of 10x synthesis buffer (5 mM each dNTP, 10 mM ATP, 100 mM Tris pH 7.4, 50 mM $MgCl_2$, 20 mM DTT), 1.3 µl T4 DNA ligase (Roche Applied Sciences, Indianapolis, Ind.), 1.3 µl diluted T7 DNA (1U/µl) polymerase (New England BioLabs, Beverly, Mass.) and incubating at 37° C. for 30 minutes.

The ligated reaction was diluted 1 part DNA to 3 parts distilled water and 1 µl electroporated into 40 µl of electrocompetent E. coli DH 10B (Invitrogen, Carlsbad, Calif.) as described in Example 8 of U.S. Pat. No. 6,057,098. The transformed sample was immediately diluted to 1 ml with 2xYT and plated at various dilutions on LB agar plates supplemented with ampicillin (100 µg/ml) (Fisher, Pittsburgh, Pa.) and grown overnight at 37° C.

Four colonies, designated AL1.1, AL1.2, AL1.3, and AL1.4, were picked and grown overnight at 37° C. in 50 ml 2xYT (100 µg/ml ampicillin). The following day glycerol freezer stocks were made for long term storage at −80° C. and plasmid purified from the remaining overnight culture using a Qiagen High-Speed Plasmid Midi Kit (Qiagen, Valencia, Calif.). The vectors were restricted with NsiI and HindIII (Roche Applied Sciences, Indianapolis, Ind.) and analyzed by agarose gel electrophoresis. All four vectors were found to contain both restriction sites.

The AL1.1, AL1.2, AL1.3, and AL1.4 vectors were tested for expression of antibody using a control antibody CD.TXA.22.2. This monoclonal came from the selection process as described in Example 15 of U.S. Pat. No. 6,057,098. The CD.TXA.22.2 plasmid was prepared from an overnight culture using a Qiagen High-Speed Plasmid Midi Kit following manufacturers' recommendations. The antibody cassette region was amplified by PCR as described in Example 18 of U.S. Pat. No. 6,057,098, using 5 ng of CD.TXA.22.2 plasmid as template with primers A and O (Table 2). The primers, in addition to having sequence specific to CD.TXA.22.2, contain approximately 20 nucleotides of vector sequence at their 5'-end corresponding to the 3'-end of the Plac and the sequence immediately downstream of the HindIII site. Additionally, primer 0 has six histidine codons, a TAA stop codon, and 19 nucleotides of tetracycline promoter between the CDTXA.22.2 coding sequence and the vector sequence (Example 17, U.S. Pat. No. 6,057,098). The PCR products were run on agarose gel electrophoresis and full-length products excised from the gel and purified as described previously. The CDTXA.22.2 insert and NsiI-HinDIII digested vectors were prepared for T4 exonuclease digestion by aliquoting 1.0 μg of each in separate tubes, adding 1.0 μl of 10x restriction endonuclease Buffer A and bringing the volume to 9.0 μl with water. The samples were digested for 4 minutes at 30° C. with 1 μl (1U/μl) of T4 DNA polymerase. The T4 DNA polymerase was heat inactivated by incubation at 70° C. for 10 minutes. The samples were cooled, briefly spun, and the digested insert (100 ng) and vector (100 ng) mixed together with 1 μl of 10x annealing buffer and the volume brought to 10 μl with water. The samples were annealed, ligated, and electroporated into electrocompetent cells as described above. The transformed cells were diluted to 1.0 ml with 2xYT broth and 1 μl, 10 μl, and 100 μl plated on LB agar plates supplemented with tetracycline (10 μg/ml) (Fisher, Pittsburgh, Pa.) and grown overnight at 37° C. Three separate picks were taken from each of the AL1 vector subtypes, and grown overnight in shake flasks. The following day glycerol freezer stocks were made for long term storage at −80° C., and the clones were named WC2. These WC2 clones were cultured and the CD.TXA.22.2 antibody purified by nickel-chelate chromatography as described in Example 3, except that expression was induced by the addition of isopropyl-B-D-thiogalactoside (IPTG) (Roche Applied Sciences, Indianapolis, Ind.) to 1 mM. On the basis of these expression results, the AL1.3 vector was chosen for future cloning experiments.

Construction of AL2.2 Expression Vector

Another expression vector similar to those described in Example 17 of U.S. Pat. No. 6,057,098 was developed for cloning proteins with or without signal sequences. The vector is a modified pBR322 plasmid, designated AL2.2, which contains a rhamnose promoter (PrhaSB), the rhaR and rhaS genes, ampicillin resistance gene, NsiI and HindIII restriction sites, and a partial tetracycline resistance gene.

A target comprising the rhaR and rhaS regulatory genes including the PrhaSB was amplified from $E.\ coli$ strain XL1-Blue (Stratagene, San Diego, Calif.) by PCR using a high-fidelity PCR system, Expand (Roche, Applied Science, Indianapolis, Ind.) with primers D and E (Table 2). The primers D and E, in addition to having sequence specific to rhaRI and PrhaSB (Genbank accession number AE000465) contain approximately 20 nucleotides of pBR322 vector sequence at their 5'-ends complementary to the 5' side of the EcoRI restriction site and the 3' side of the HindIII restriction site, respectively. This complementary sequence will facilitate cloning the rha insert (rhaR rhaS PrhaSB) into the pBR322 backbone.

The rhamnose PCR template was prepared by centrifuging 100 μl of overnight XL1 culture and resuspending the pellet in 1 ml of distilled water. The cell suspension was washed three times with distilled water. The final pellet was resuspended in 100 μl of distilled water and incubated at 95° C. for five minutes. Four 100 μl PCR reactions were performed, each containing 100 pmol of primer D, 100 pmol of primer E, 2 units of Expand polymerase, 10 μl 2 mM dNTPs, 10 μl 10x Expand reaction buffer, 1, 2, or 4 μl heat-denatured $E.\ coli$ stock as template, and water to 100 μl. The reaction was carried out in a Perkin-Elmer thermal cycler (Model 9600) using the following thermal profile: one cycle of denaturation at 94° C. (1 minute); ten cycles of denaturation (15 sec, 94° C.), annealing (30 sec, 55° C.), elongation (120 sec, 72° C.); twenty cycles of denaturation (15 sec, 94° C.), annealing (30 sec, 55° C.), elongation (140 sec plus 20 sec for each additional cycle, 72° C.); elongation (6 min, 72° C.); soak (4° C., forever). The rha PCR product was verified by agarose gel electrophoresis. The reactions were pooled, and purified with a QiaQuick column as per manufacturers' recommendations. The concentration of the insert was determined by $A_{260}$.

The rha insert and EcoRI/HindIII linearized pBR vector (see preparation of AL1.3 expression vector described above) were prepared for T4 exonuclease digestion by adding 1.0 μl of 10x Buffer A to 1.0 μg of DNA and bringing the final volume to 9 μl with water. The samples were digested for 4 minutes at 30° C. with 1 μl (1U/μl) of T4 DNA polymerase. The T4 DNA polymerase was heat inactivated by incubation at 70° C. for 10 minutes. The samples were cooled, briefly spun. In a separate tube, 100 ng of the digested rha insert, 100 ng of digested vector, and 1.0 μl of 10x annealing buffer were added and the volume brought to 10 μl with water. The samples were annealed, ligated, and electroporated into electrocompetent cells as described above. The transformed cells were diluted to 1.0 ml with 2xYT broth and plated at various dilutions on LB agar plates supplemented with ampicillin (100 μg/ml) and grown overnight at 37° C.

Ten clones were picked and suspended in 30 μl 2xYT. These clones were tested for the correct insert by PCR amplification with primers D and E (Table 2), using 1 μl of the suspended bacteria as template. Agarose gel electrophoresis of the PCR reactions demonstrated that nine of the ten clones had the rha insert. Four of the positive clones were picked and grown overnight 37° C. in 50 ml LB broth supplemented with ampicillin at 100 μg/ml. The following day glycerol freezer stocks were made for long term storage at −80° C. and plasmid purified from the remaining overnight cultures using a Qiagen High-Speed Plasmid Midi Kit following manufacturers' recommendations. The plasmids, 1 μg, were treated with NsiI and HindIII restriction enzymes. Agarose gel electrophoresis of the digests indicated that three of the constructs had both sites. These new vectors, AL2.1, AL2.2, and AL2.3, contained the rhaR and rhaS genes and the PrhaSB promoter, ampicillin resistance gene, a partial tetracycline resistance gene, and NsiI and HindIII restriction sites. The sequence of the rha insert in these vectors was verified at MacConnell Research (San Diego, Calif.) by the dideoxy chain termination method using a Sequatherm sequencing kit (Epicenter Technologies, Madison, Wis.) and a LI-COR 4000L automated sequencer (LI-COR, Lincoln, Nebr.) using oligonucleotide primers J, K, and N (Table 2). On the basis of these sequence results, AL2.2 was chosen for use as the expression vector.

The control antibody CDTXA.22.2 was cloned into AL2.2 by a process identical to that for the AL1.3 vector described above, except that primer F (Table 2) was substituted for primer A in the PCR amplification portion of the process. The CDTXA.22.2 clone, WC23, was cultured, induced with rhamnose, and the CDTXA.22.2 antibody successfully purified by nickel-chelate chromatography as described in Example 3.

The AL2.2 vector, 10 ug, was restricted with NsiI and HindIII and fractionated by agarose gel electrophoresis, full-length products excised from the gel, and purified with a QiaQuick column as per manufacturers' recommendations. The concentration of vector was determined by $A_{260}$. The vector was prepared to receive insert by T4 digestion as described previously.

pBRSacI/HindIII (pBRsaCH3) Expression Vector

The pBRSaCH3 vector was derived from AL2.2. It is identical to AL2.2 in every respect except that the NsiI site has been replaced with the human ceruloplasmin signal sequence. The last two bases at the 3' end of the ceruloplasmin signal sequence have been modified to create a SacI restriction. The SacI and HindIII sites allow the vector to be linearized in preparation for receiving insert. It was made for cloning antibodies and antigens that use the human ceruloplasmin signal sequence at the 5'-end of the construct. By placing the signal sequence on the vector, the PCR primers for subcloning can be much smaller. As such, the PCR reactions are more efficient. Fewer reactions are required resulting in a reduction in both time and resources needed.

PCR primers were made corresponding to the coding sequence at the 5' and 3'-ends of the r-methamphetamine (rMET 10) kappa chain, primers AA and U, respectively (Table 2). This monoclonal came from the selection process as described in Example 4. The rMET10 plasmid was prepared from an overnight culture using a Qiagen High-Speed Plasmid Midi Kit following manufacturers' recommendations. In addition to the kappa chain coding sequence, the 5' primer contains approximately 20 nucleotides of vector sequence at its 5'-end corresponding the region upstream of the NsiI site in the AL2.2 vector, followed by sequence coding for the human ceruloplasmin signal sequence. The last codon of the ceruloplasmin signal sequence has been modified to form, together with the penultimate codon, a SacI restriction site. The 3' primer contains approximately 20 nucleotides of vector sequence 3' to the HindIII site at its 5' end followed by sequence corresponding to the 3'-end of the kappa chain coding sequence. The PCR reactions were performed as described above using 5 ng of rMET10 plasmid as template. The PCR product was verified by agarose gel electrophoresis. The reactions were pooled, and the ceruloplasmin-SacI insert purified with a QiaQuick column as per manufacturers' recommendations. The concentration of the insert was determined by $A_{260}$.

The AL2.2 vector was prepared for the ceruloplasmin-SacI insert by digestion with NsiI and HindIII as described above, and along with the ceruloplasmin-SacI insert T4 digested, annealed, electroporated into DH10B, and plated as described above. Three colonies were picked and grown overnight at 37° C. in 50 ml 2×YT broth supplemented with ampicillin at 100 μg/ml. The following day glycerol freezer stocks were made for long term storage at −80° C. and plasmid purified from the remaining overnight culture using a Qiagen High-Speed Plasmid Midi Kit following manufacturers' recommendations. The plasmids were digested with SacI and HindIII restriction enzymes (Roche Applied Sciences, Indianapolis, Ind.) as recommended by the manufacturer. Agarose gel electrophoresis of the digests indicated that all three of the constructs had both sites. These new vectors, pBRsaCH3.1, pBRsaCH3.2, pBRsaCH3.3 contain the rhaR and rhaS genes and the PrhaSB promoter, the human ceuloplasmin signal sequence, ampicillin resistance (beta-lactamase) gene, a partial tetracycline resistance gene, and SacI and HindIII restriction sites. The sequence of the three vectors was verified at Macconnell Research as described in Example 1 using primer N (Table 2).

Example 2

Selection of Eukaryotic Signal Sequences

Eukaryotic signal sequences were selected and incorporated into expression vectors with polynucleotides encoding polypeptides, including antibody heavy and light chain polypeptides as described herein.

A total of twenty different eukaryotic signal sequences (Table 1) were used to replace the pectate lyase (pelB) signal sequence on a control antibody, CDTXA.22.2 (Example 15 of U.S. Pat. No. 6,057,098). The resulting clones had an eukaryotic signal sequence directing secretion of the kappa chain and a prokaryotic signal sequence, alkaline phosphatase (alkP), directing secretion of the heavy chain. The alkP signal sequence was used for the heavy chain so that the eukaryotic signal sequences linked to the kappa chain could be analyzed independently for efficient expression and secretion, as well as complete processing by SDS-PAGE analysis.

The 5'-primers corresponding to the twenty eukaryotic signal sequences in Table 1 all contained approximately 20 nucleotides at their 5'-end corresponding to the 3'-end of the lac promoter in vector AL1.3 (Example 1), followed by the sequence coding for each of the eukaryotic signal sequences in frame with the first twenty nucleotides corresponding to the 5'-end of the mature CDTXA.22.2 kappa chain. The codons chosen to encode these signal sequences were based in part on the preferential codon usage observed for highly expressed genes in enteric bacteria (The Wisconsin Package, by Genetics Computer Group, Inc.) and to a lesser extent, they were designed to minimize the potential for any secondary structure (Humphreys et.al., Protein and Purification 20, 252-264 (2000)) as both can potentially effect levels of expression. As such, the codons used in these sequences differed somewhat from those used in their native organisms. Twenty antibody DNA cassettes corresponding to the twenty different eukaryotic signal sequences were amplified individually using the 5' primers described above, the 3' primer 0 (Table 2) previously described, and 5 ng of CDTXA.22.2 plasmid (Example 1) as template using Expand DNA Polymerase as described in Example 18 of U.S. Pat. No. 6,057,098. The PCR products were run on agarose gel electrophoresis, and full-length inserts were excised and purified as described in Example 1.

The eukaryotic signal sequence antibody cassettes, together with the control clone WC2 (Example 1), which utilizes pelB and alkP secretory signals on the kappa and heavy chains, respectively, were modified for introduction into the more tightly regulated vector AL2.2 under the PrhaSB promoter to generate the clones that would be used to express antibody for SDS-PAGE gel analysis. This was accomplished by amplifying the antibody cassette from a WC2 culture and re-amplifying the eukaryotic signal sequence antibody cassettes using primers H and O (Table 2) using 1 μl of heat-denatured WC2 cell stock and 5 ng of the purified eukaryotic signal sequence antibody cassettes as template, respectively, and Expand DNA Polymerase as described in Example 18 of U.S. Pat. No. 6,057,098. Primer H contains AL2.2 vector sequence at its 5'-end corresponding to the 3'-end of the PrhaSB, followed by sequence specific to the 3'-end of the lac promoter.

The antibody cassette and AL2.2 vector were annealed, electroporated, and plated as described in Example 1. These clones retained their original WC designations followed by an 'A' to designate the AL2.2 vector. The WC2A-22A clones were grown, induced, and antibody purified as described in Example 3.

TABLE 1

Eukaryotic signal sequences

| Plasmid Clone* | Signal Sequence Description | Accession # |
|---|---|---|
| WC3 | CarboxypeptidaseY (*Saccharomyces cerevisiae*) | M15482.1 |
| WC4 | KRE5 protein (*Saccharomyces cerevisiae*) | M3356.1 |
| WC5 | Apolipoprotein C-1 Precursor (rat) | APC1_RAT |
| WC6 | Arylsulfatase precursor (*Chlamydomonas reinhardtii*) | ARS_CHLRE |
| WC7 | Clara cells 10kd secretory protein precursor (human) | 10KS_HUMAN |
| WC8 | Chromogranin A precursor (human) | CMGA_HUMAN |
| WC9 | Neutrophil defensin 1,2,3 precursor (human) | DEFN_HUMAN |
| WC10 | Beta-hexosaminidase a-chain precursor (human) | HEXA_HUMAN |
| WC11 | SPARC precursor (human) | SPRC_HUMAN |
| WC12 | Tumor necrosis factor precursor 2 (human) | TNR2_HUMAN |
| WC13 | Lambda'CL (murine) | Ref. A |
| WC14 | Kappa 6A4'CL (murine) | Ref. B |
| WC15** | Cyst wall protein 1 (*Giardia lamblia*) | U09330 |
| WC16 | Kappa chain 3-13'CL (murine) | Ref. C |
| WC17 | Glycoprotein antigen BM86 precursor (cattle tick) | BM86_BOOMI |
| WC18 | Carbonic anhydrase 2 precursor (*Chlamydomonas rein.*) | CAH2_CHLRE |
| WC19 | Ceruloplasmin precursor (human) | CERU_HUMAN |
| WC20 | Glycolipid anchored surface protein precursor (yeast) | GAS1_YEAST |
| WC21 | Interleukin-6 Receptor precursor (rat) | IL6R_RAT |
| WC22 | Repressible acid phosphatase precursor (yeast) | PPA5_YEAST |

*The clones have an 'A' appended onto the end of the name if they are in the AL2.2 vector under the control of the rhaSB promoter.
**The PCR amplification resulted in less than full-length insert and WC15 was eliminated from the study.

References:
A Bernard et al. (1978) CELL, 15, pp. 1133-1144.
B Marget et al. (1988) GENE, 74, pp. 335-345.
C Bedzyk et al. (1990) JBC, 265, pp. 133-138.

TABLE 2

PCR and sequencing primer sequence (SEQ ID NOS: 4-42)

A- 5' (CGCCAAGGAGACAGTCATAATGAAATACCTATTGCCTACGGC)

B- 5' (GTGATAAACTACCGCATTAAAGCTTGCGTCATTTACCTACTTAAGATCCTCAATGCATTATGACTGTCT
CCTTGGCG)

C- 5' (CCTTTCGTCTTCAAGAATTCGTGAGTTAGCTCACTCATTAGG)

D- 5' (CCCTTTCGTCTTCAAGAATTCTTAATCTTTCTGCGAATTGAGATG)

E- 5' (GTGATAAACTACCGCATTAAAGCTTGCGTCATTTACCTACTTAAGATCCTCAATGCATAATGTGATCCT
GCTGAATTTC)

F- 5' (GAAATTCAGCAGGATCACATTATGAAATACCTATTGCCTACGGC)

G- 5' (ATGTACAAAGCGTGGGTAACGC)

H- 5' (ACTGGTCGTAATGAAGCCAAGGAGACAGTCATAATG)

I- 5' (GCGTAGGAGTGTTTATCGTCAGC)

J- 5' (CACCTGACGTCTAAGAAACC)

K- 5' (CATTTTCCTGTCAGTAACGAG)

L- 5' (AGTGCCAAGTGACGCGTTCTA)

M- 5' (GCAACTGTTGGGAAGGG)

N- 5' (GAGGATGACGATGAGCGC)

O- 5' (GTGATAAACTACCGCATTAAAGCTTATCGATGATAAGCTGTCAATTAGTGATGGTGATGGTGATGAGAATC)

P- 5' (TTCTAGAACGCGTCACTTGGC)

Q- 5' (GCCAAGTGACGCGTTCTAGAATTAAGACTCATTCCTGTTGAAGCTCTT)

R- 5' (GTGATAAACTACCGCATTAAAGCTTATCGATGATAAGCTGTCAATTAGTGATGGTGATGGTGATGATG
AGAATC)

S- 5' (GAAATTCAGCAGGATCACATTATGAAAATCCTGATTCTCGGTATCTTCCTGTTTCTCTGTTCTACTCC
AGCTTGGGCAGAAAATGTGCTCACCCAGTCTG)

TABLE 2-continued

PCR and sequencing primer sequence (SEQ ID NOS: 4-42)

T- 5' (CTTTGTACATGGAGAAAATAAAATGAAGATTCTTATCCTGGGCATTTTTCTTTTCCTGTGCAGCACAC
CAGCATGGGCTGATGTGCAGCTTCAGGAGTCTC)

U- 5' (GTGATAAACTACCGCATTAAAGCTTCTCATTCCTGTTGAAGCTCTTG)

V- 5' (GTTGCACTGCAGGCTCAAGCGGATGTGCAGCTTCAGGAGTCGGG)

W- 5' (CTCTGTTCTACTCCAGCTTGGGCA)

X- 5' (CTCTGTTCTACTCCAGCTTGGGCAGAAAATGTGCTCACCCAGTCTCC)

Y- 5' (GTGATAAACTACCGCATTAAAGCTTATCGATGATAAGCTGTCAATTATGGATTTTGATTCTCAGCCCT
CTTCACAAACTTCTCCACAACCCTCTGCACCCATGGTTC)

Z- 5' (CTCTGTTCTACTCCAGCTTGGGCACACCATCACCATCACCATCACGACGATGACGATAAAAGTGCTAA
AGAACTTAGATGTGAGTGC)

AA- 5' (GAAATTCAGCAGGATCACATTATGAAAATCCTGATTCTCGGTATCTTCCTGTTTCTCTGTTCTACTCC
AGCTTGGGAGCTCGAAAATGTGCTCACCCAGTCTCC)

BB- 5' (CATCACGAGCTCAGTGTGCCAGAGGTTGAATATGACTGCCTCC)

CC- 5' (AAGCTGCACATCCATGCACAGATTCCGTTTATTTTCTCCATG)

DD- 5' (GTCTGGGTCATCACGAGCTCCCAAGCTGGAGTAGAACAGAGAAACAGGAAGATACCCCGAGAATCAG
GATTTTCATTATGACTGTCTCCTTGGCGT)

EE- 5' (GACTCCTGAAGCTGCACATCCGCTTGAGCCTGCAGTGCAACAAGCAGAATAGCTGCAAGGATAGCCAG
AGTACGCATTTTATTTTCTCCATGTACAAAGCG)

FF- 5' (AGGTGTCGTAAGCTTGAATTCAGACACCTCTGCCGCCACCATGAG)

GG- 5' (GGGCTGGCTTACCTGCGGCCTTAGTGATGGTGATGGTGATGGTCCTCAGGGCACTGCAGGATG)

HH- 5' (TTCTCAAGCCTCAGACAGTG)

II- 5' (CCTGGATGCAGGCTACTCTAG)

JJ- 5' (GCAACTCTCTACTGTTTCTCC)

KK- 5' (TCGCTGCCCAACCAGCCATG)

LL- 5' (ACCCGTTTTTTTGGATGGAGTGAAACGATGAAACAAAGCACTATTGCACTG)

MM- 5' (GCCAAAACGACACCCCCATC)

Example 3

Evaluation and Selection of Eukaryotic Signal Sequences

A variety of eukaryotic signal sequences were evaluated and selected for expression of polypeptides in host cells, including for the expression of antibody heavy or light chain polypeptides in host cells as described herein. The polypeptides were expressed in cultured host cells, including in bacterial host cells via an inducible rhamnose promoter. Testing included evaluating the expression (e.g., yield, quantity) of the polypeptide and the processing (e.g., cleavage) of the signal sequence from the polypeptide. Detectable expression including, for example, by a detectable SDS-PAGE analysis and evidence of processing of the signal sequence from the polypeptide, including for example, as evidenced by SDS-PAGE analysis, allowed the selection of eukaryotic signal sequences for expression. Preferred eukaryotic signal sequences were those which yielded efficient expression (e.g., detectable, not very faint and preferably strong, polypeptide bands by SDS-PAGE) and effective and/or complete processing (e.g., faster migration of polypeptide chain bands, indicating processing of signal sequence and/or for each polypeptide chain expressed, the presence of a single band, not two or more, indicating complete processing of signal sequence). A variety of methods for detecting expression and/or processing are known by and useful to those skilled in the art, including SDS-PAGE methods described herein.

Evaluation of Eukaryotic Signal Sequences on CD.TXA.22.2 Antibody Expression Levels Twenty sets of clones containing different plasmids, WC2A-WC22A, were constructed as described in Example 2 and used to express the anti-C. difficile toxin A antibody CDTXA.22.2 with an inducible rhamnose promoter. In all cases, the heavy chain was engineered with a prokaryotic alkaline phosphatase signal sequence. In the control set, WC2A, the kappa chain was engineered with a prokaryotic pelB signal sequence, while in the remaining nineteen, it was engineered with nineteen distinct eukaryotic signal sequences. In all cases, the antibody heavy chain was also engineered with a hexahistidine tag on the C-terminus to allow for affinity purification. The plasmids contained tetracycline and ampicillin resistance genes to allow for selection during culture. These plasmids were electroporated into *E. coli* strain DH10B rha$^+$ (Invitrogen, Carlsbad, Calif.). Three clones from each set were evaluated for expression of the CDTXA.22.2 antibody.

Shake flasks were inoculated with cells from −70° C. cell banks and grown overnight at 37° C. in an Innova 4330 refrigerated incubator shaker (New Brunswick Scientific, Edison, N.J.). The cells were cultured in a semi-defined culture medium (Pack, P. et. al. 1993. Bio/Technology 11: 1271-1277) supplemented with 0.3 g/L L-leucine, 0.3 g/L L-isoleucine, 12 g/L casein enzymatic hydrolysate (ICN Biomedicals, Costa Mesa, Calif.), 12.5 g/L glycerol. The medium was supplemented with 10 µg/mL tetracycline to maintain selection. The inocula were used to seed 500 mL shake flasks that were also grown at 37° C. Protein expression was induced by addition of L-rhamnose (Sigma, St. Louis, Mo.) at desired concentrations during the logarithmic growth phase, following which, the temperature was controlled at 23° C. After batch termination, the cultures were adjusted to pH 7 and supplemented with imidazole to 10 mM. The cultures were then homogenized at 17000 psi in a M-110Y microfluidizer (Microfluidics, Newton, Mass.).

Chelating Sepharose FF resin (Amersham Pharmacia Biotech, Piscataway, N.J.) was charged with 0.1 M $NiCl_2$ and equilibrated in 20 mM borate, 150 mM NaCl, 10 mM imidazole, 0.01% $NaN_3$, pH 8.0 buffer. The 500 mL culture homogenates were each incubated with 5 mL of resin in an incubator shaker at room temperature. The homogenate/resin mixtures were then poured into disposable chromatography columns fitted with funnels. The resin was allowed to settle in the columns and the homogenates aspirated with a vacuum pump. After re-equilibration, the columns were eluted with 20 mM borate, 150 mM NaCl, 200 mM imidazole, 0.01% $NaN_3$, pH 8.0 buffer. Next, disposable chromatography columns were each packed with 2 mL of Protein G Sepharose FF resin (Amersham Pharmacia Biotech, Piscataway, N.J.). The columns were equilibrated in 20 mM Borate, 150 mM NaCl, 0.01% $NaN_3$, pH 8.0. The elutions from the first purification step were loaded on the Protein G columns. After re-equilibration, the columns were eluted with 0.1 M Glycine, 0.01% $NaN_3$, pH 3.0 buffer. The Protein G elutions were then immediately supplemented with NaCl to 150 mM and neutralized to pH 8.0 with 1 M Tris, pH 10.2 buffer. The purified antibodies were stored at 4° C.

The purified antibodies were evaluated for yields and banding patterns by SDS-PAGE analysis, using 12% Tris-glycine gels (Invitrogen, Carlsbad, Calif.). The following criteria were used to reject candidate clones and therefore the corresponding eukaryotic signal sequences:
 (a) the absence of bands on the gel, indicating undetectable antibody expression;
 (b) very faint bands on the gel, indicating unacceptably poor antibody expression;
 (c) slow migration of the kappa chain bands, indicating no processing of signal sequence;
 (d) the presence of two or more kappa chain bands, indicating incomplete processing of signal sequence.

On this basis, only the following three eukaryotic signal sequences met the selection criteria:
 Human Ceruloplasmin Precursor
 Human neutrophil defensin 1,2,3 precursor
 *Chlamydomonas* reinhardtii arylsulfatase precursor Complete processing for these three eukaryotic signal sequences was confirmed by performing N-terminal amino acid sequencing on the kappa chain using Perkin Elmer Applied Biosystems Model 494 Procise protein/peptide sequencer (PE Applied Biosystems, Foster City, Calif.). The polynucleotide sequences of these three signal sequences is shown in Table 3.

TABLE 3

| Sequences of Eukaryotic Signal Sequence Clones Meeting Selection Criteria |
|---|
| WC6: Arylsulfatase precursor (*Chlamydomonas reinhardtii*) signal sequence (SEQ ID NO: 46): |
| 5'-(ATGGGTGCTCTGGCAGTTTTCGCTGTAGCGTGTCTGGCAGCCGTTGCGTCTGTAGCTCACGCA) |
| WC9: Neutrophil defensin 1,2,3 (human) signal sequence (SEQ ID NO: 45): |
| 5'-(ATGCGTACTCTGGCTATCCTTGCAGCTATTCTGCTTGTTGCACTGCAGGCTCAAGCG) |
| WC19: Ceruloplasmin precursor (human) signal sequence (SEQ ID NO: 43): |
| 5'-(ATGAAAATCCTGATTCTCGGTATCTTCCTGTTTCTCTGTTCTACTCCAGCTTGGGCA) |

Example 4

Preparation of Monoclonal Antibodies

Monoclonal antibodies, including for an rMET1 and an rMET.10 antibody as described herein, were selected and prepared.

Preparation of rMET1 and rMET10 Monoclonal Antibodies

Synthesis of P-(3-mercaptopropyl)amino-d-methamphetamine

P-(3-mercaptopropyl)amino-d-methamphetamine (reduced methamphetamine derivative) can be synthesized as described in Example 11 of U.S. Pat. No. 5,470,997.

Preparation of Conjugates of Reduced Methamphetamine Derivative

Conjugates of reduced methamphetamine derivative with keyhole limpet hemocyanin, bovine serum albumin and alkaline phosphatase were prepared as follows.

Keyhole limpet hemocyanin (KLH, Calbiochem, San Diego, Calif.) was reacted with sulfosuccinimidyl 4-(N-maleimidomethyl)cyclohexane-1-carboxylate (SULFO-SMCC) (Pierce Chemical Co., Rockford, Ill.) by adding SULFO-SMCC and maintaining the pH between 7 and 7.5 with 1N potassium hydroxide over a period of one hr at room temperature while stirring. The protein was separated from the unreacted SULFO-SMCC by gel filtration chromatography in 0.1 M potassium phosphate, 0.02 M potassium borate, and 0.15 M sodium chloride, pH 7.0. The reduced methamphetamine derivative was added to the KLH-maleimide in substantial molar excess over the estimated maleimide amounts present and the solution was stirred for 4 hr at 4° C. and then dialyzed against 3 volumes of one liter of pyrogen-free phosphate-buffered saline, pH7.4, prior to immunization.

Alkaline phosphatase (AP, Calzyme Laboratories, San Luis Obispo, Calif.) was placed into dialysis versus a minimum of 100 volumes of column buffer (50 mM potassium phosphate, 10 mM potassium borate, 0.15 M sodium chloride, 1 mM $MgSO_4$, pH 7.0) at 2-8° C. for at least 4 hr. The buffer was changed at least twice prior to use of the AP. When the AP was removed from dialysis and brought to room temperature, the concentration was determined by absorbance at 280 nm using an absorbance of 0.77 for a 1 mg/mL solution. The AP was diluted to 5 mg/mL with column buffer. The reaction of AP and succinimidyl 4-(N-maleimidomethyl)cyclohexane-1-carboxylate (SMCC)) (Pierce Chemical Co., Rockford, Ill.) was carried out using a 20:1 ratio of SMCC: AP. SMCC was dissolved in acetonitrile at 20 mg/mL and added to AP while vortexing or rapidly stirring. The solution was allowed to stand at room temperature for 90 min before the unreacted SMCC and low molecular weight reaction products were separated from the AP using gel filtration chromatography (G50 Fine, Pharmacia Biotech, Piscataway, N.J.) in a column equilibrated with column buffer. The reduced methamphetamine derivative was added to the AP-SMCC in substantial molar excess over the estimated maleimide amounts present and the solution was incubated at room temperature for at least 1 hr and then dialyzed against 3 volumes of 20 mM potassium borate, 0.15 M sodium chloride, 1 mM $MgSO_4$, pH 8.0. The methamphetamine-AP was biotinylated as described in Example 9 of U.S. Pat. No. 6,057,098.

BSA was biotinylated as described in Example 9 of U.S. Pat. No. 6,057,098. The biotinylated BSA was reacted with SMCC by adding a solution of SMCC in acetonitrile to the BSA at a molar ratio of 1:10 BSA:SMCC and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. Reduced methamphetamine was added to the BSA-SMCC in substantial molar excess over the estimated maleimide amounts present and the solution was stirred for at least 1 hr at room temperature. Unreacted material was removed by extensive dialysis into 0.1M potassium phosphate, 0.02 M potassium borate, 0.15 M sodium chloride, pH 7.0.

Preparation of BSA-SMCC

Bovine serum albumin (BSA, 20 mg/ml) was reacted with SMCC by adding a solution of SMCC in acetonitrile to the BSA at a molar ratio of 1:50 BSA:SMCC and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. Beta mercaptoethanol (Fisher Scientific, Pittsburgh, Pa.) was added to the BSA-SMCC in substantial molar excess over the estimated maleimide amounts present and the solution was stirred for at least 1 hr at room temperature. Free mercaptoethanol was removed by extensive dialysis into 0.1M potassium phosphate, 0.02 M potassium borate, 0.15 M sodium chloride, pH 7.0.

Selection of rMet1 from a Phage Display Library

A phage display library was made using RNA purified from the spleen of one mouse immunized with the reduced methamphetamine KLH as described in Examples 1-4 and 7 of U.S. Pat. No. 6,057,098 using BS45 uracil template. The antibody phage binding to the reduced methamphetamine AP biotin conjugate were selected as described in Example 15 of U.S. Pat. No. 6,057,098. A large excess of BSA-SMCC over the reduced methamphetamine AP biotin was added to the antibody phage during several rounds of panning to remove any antibodies specific to the SMCC linker. After the fifth round of panning, the antibody phage were incubated with the reduced methamphetamine AP biotin, and a large excess of several drugs to remove methamphetamine antibodies that were cross-reactive with these drugs. The cross-reacting drugs added were +ephedrine, −ephedrine, d-pseudoephedrine, ranitidine, procainamide, phenmetrazine, and trimethobenzamide. Two rounds of selection were done in the presence of these cross-reactants. An aliquot of the phage binding to the avidin latex in the presence of the cross-reactants was plated on 100 mm LB plates and the plaques were overlayed with nitrocellulose filters as described in Example 15 of U.S. Pat. No. 6,057,098. The filters were developed with AP-reduced methamphetamine conjugate as described in Example 15 of U.S. Pat. No. 6,057,098. Positive plaques were subcloned into the pBRncoH3 expression plasmid as described in Example 18 of U.S. Pat. No. 6,057,098. One of those clones was designated as rMET 1.

Antibody rMET10 is the same antibody sequence as rMet1, but the decapeptide sequence at the 3' end of the kappa chain was deleted. Using rMet1 frozen stock cells as template (see Example 1), two PCR reactions were performed using Expand DNA polymerase (Example 18 of U.S. Pat. No. 6,057,098). The first reaction was done using oligonucleotides KK and Q (Table 2). The second reaction was done using oligonucleotides P and O (Table 2). Both PCR products were purified, digested with T4 DNA polymerase and subcloned into pBRncoH3 as described in Example 18 of U.S. Pat. No. 6,057,098. The rMet1 and rMet10 clones were sequenced at MacConnell Research (San Diego, Calif.) by the dideoxy chain termination method using a Sequatherm sequencing kit (Epicenter Technologies, Madison, Wis.) and a LI-COR 4000L automated sequencer (LI-COR, Lincoln, Nebr.). Oligonucleotide primers JJ and N (Table 2), that bind on the 5' side of the kappa chain and 3' side of the heavy chain respectively, were used.

Example 5

Cloning into Expression Vectors

Polynucleotides encoding polypeptides, including encoding an rMET10 monoclonal antibody as described herein, were cloned into expression vectors.

Cloning of the r-Methamphetamine10 (rMET10) Antibody into the AL2.2 Vector using the Human Ceruloplasmin Signal Sequence (SEQ ID NO:1) on both the Kappa and Heavy Chains The monoclonal rMET10 came from the selection and cloning process as described in Example 4. In its original configuration, pelB and alkaline phosphatase signal sequences were used to direct secretion of the kappa and heavy chain, respectively. In order to convert these signal sequences to the human ceruloplasmin signal sequence, the kappa chain and heavy chain were amplified separately and then reassembled in a kappa chain-heavy chain cassette during the subcloning process. The kappa chain was amplified using primers S and G (Table 2). Primer S, in addition to having sequence specific to rMET10, contains approximately 20 nucleotides of AL2.2 vector sequence at its 5'-end corresponding to the 3'-end of the PrhaSB followed by sequence coding for the human ceruloplasmin signal sequence in frame with the kappa chain. Primer G binds to a region in the phage-display vector that is downstream of the kappa chain stop codon and upstream of the heavy chain ribosome binding site. The heavy chain was amplified using primers T and R (Table 2). Primer T, in addition to having sequence specific to rMET10, contains approximately 20 nucleotides complementary to primer G at its 5'-end followed by sequence coding for the human ceruloplasmin signal sequence in frame with the heavy chain.

In order to minimize the chance of recombination, the nucleotide sequence used for the heavy and kappa chain ceruloplasmin signal sequence (Table 4) differ as much as possible in the actual codons used while still taking into account E. coli codon usage. The kappa chain and heavy chain were amplified in separate PCR reactions using 5 ng of rMET10 plasmid as template, purified, and T4 digested in preparation for cloning as described in Example 18 of U.S. Pat. No. 6,054,098. The rmet10 plasmid was prepared from an overnight culture of a rMET10 clone (Example 4) using a Qiagen High-Speed Plasmid Midi Kit following manufacturers' recommendations. Following T4 digestion, the samples were cooled, briefly spun, and 50 ng each of the kappa and heavy chain digested insert added to 100 ng of digested AL2.2 vector in a fresh microfuge tube. After the addition of 1.0 µl of 10x annealing buffer, the volume was brought to 10 µl with water and the mixture heated to 70° C. for 2 minutes and cooled over 20 minutes to room temperature to allow the insert and vector to anneal. The annealed DNA was diluted one to three with distilled water and 1 µl electroporated (Example 8 of U.S. Pat. No. 6,057,098) into 40 µl of electrocompetent E. coli strain DH10B and plated as described in Example 12. Colonies were picked and grown overnight in 50 ml 2×YT (20 µg/ml tetracycline) at 37° C. The following day glycerol freezer stocks were made for clone rMET.10.LS. 1 for long term storage at −80° C. and plasmid purified from the remaining overnight culture using Qiagen High-Speed Plasmid Midi Kit following manufacturers' recommendations. The sequence was verified at Macconnell Research as described in Example 1 using primers K and N (Table 2). The clone rMET10.LS.1 was expressed and successfully purified by nickel-chelate chromatography as described in Example 6.

TABLE 4

Selected Eukaryotic Signal Sequences used in Expression Studies

1. Expression of rMET10: Ceruloplasmin precursor (human) on both the heavy and kappa chain Kappa chain (SEQ ID NO: 43)

5'-(ATGAAAATCCTGATTCTCGGTATCTTCCTGTTTCTCTGTTCTACTCCAGCTTGGGCA)

Heavy chain (SEQ ID NO: 44)

5'-(ATGAAGATTCTTATCCTGGGCATTTTTCTTTTCCTGTGCAGCACACCAGCATGGGCT)

2. Expression of rMET1: Ceruloplasmin precursor (human) on kappa chain; Neutrophil defensin 1, 2, 3 (human) on heavy chain Kappa Chain: (SEQ ID NO: 43)

5'-(ATGAAAATCCTGATTCTCGGTATCTTCCTGTTTCTCTGTTCTACTCCAGCTTGGGCA)

Heavy chain: (SEQ ID NO: 45)

5'-(ATGCGTACTCTGGCTATCCTTGCAGCTATTCTGCTTGTTGCACTGCAGGCTCAAGCG)

3. Expression of Macaque IL-8: Ceruloplasmin precursor (human) (SEQ ID NO: 43):

5'-(ATGAAAATCCTGATTCTCGGTATCTTCCTGTTTCTCTGTTCTACTCCAGCTTGGGCA)

Example 6

Dose Studies for Expression

Dose studies for expression of polypeptides, including an rMET10 antibody as described herein, were conducted.

L-Rhamnose Dose Studies for Expression of rMET10 Antibody in Two E. coli Strains A plasmid for expressing the rMET10 antibody was constructed as described in Example 5. The kappa and heavy chains in this construct were both engineered with human ceruloplasmin signal sequence. This plasmid was electroporated into E. coli strain DH10B rha+ to generate clone rMET10.LS. 1, which was cultured under 10 µg/mL tetracycline selection. The plasmid was also electroporated into another E. coli strain ECL339 rha− (ATCC), to generate clone rMET10.ECL.20. This clone was cultured under 100 µg/mL ampicillin selection, since the host strain contains a genomic tetracycline resistance gene.

Replicate 500 mL shake flask cultures for these two clones were induced with different concentrations of L-rhamnose. A lower dose of L-rhamnose was required to induce the ECL339 rha− cells, since this sugar is not metabolized by this strain. The antibodies were purified following procedures described in Example 3. The concentrations of the antibodies were determined by measuring absorbance at 280 nm in an UV-1201 spectrophotometer (Shimadzu, Columbia, Md.) and using an extinction coefficient of 1.6 (mL)/(mgcm). The antibodies were evaluated for activity by functional ELISA assay. The biotinylated target antigens (Example 4) were coated in 96-well Neutravidin™ plates (Pierce Endogen, Rockford, Ill.). The sample antibodies were captured and then labeled with goat anti-(mouse kappa)-alkaline phosphatase (Southern Biotechnology Associates, Birmingham, Ala.).

Finally, ELISA amplification reagents (Invitrogen, Carlsbad, Calif.) were used to generate colorimetric signals. Endpoint readings at 490 nm were measured in a Vmax plate reader (Molecular Devices, Sunnyvale, Calif.) and the data analyzed using SOFTmax® PRO (Molecular Devices, Sunnyvale, Calif.). The purified antibody yields are tabulated for comparison in Table 5. For the antibodies produced at optimal rhamnose concentrations, the ELISA standard curves are plotted in FIG. 1.

Example 7

Additional Dose Studies for Expression

Additional dose studies for expression of polypeptides, including for an rMET1 antibody as described herein, were conducted.

L-Rhamnose Dose Studies for Expression of rMET1 Antibody in Two E. coli Strains

The plasmid pBRsaCH3 (Example 1) was used for cloning the rMET1 antibody (Example 9). In this case, the kappa and heavy chains were engineered with human ceruloplasmin and human neutrophil defensin signal sequences, respectively (Example 9). This plasmid was electroporated into E. coli strain DH10B rha$^+$ to generate clone rMET1.LS. 1, which was cultured under 10 µg/mL tetracycline selection. The plasmid was also electroporated into E. coli strain ECL339 rha$^-$ to generate clone rMET1.ECL. 1 which was cultured under 100 µg/mL ampicillin selection.

Figure 2:
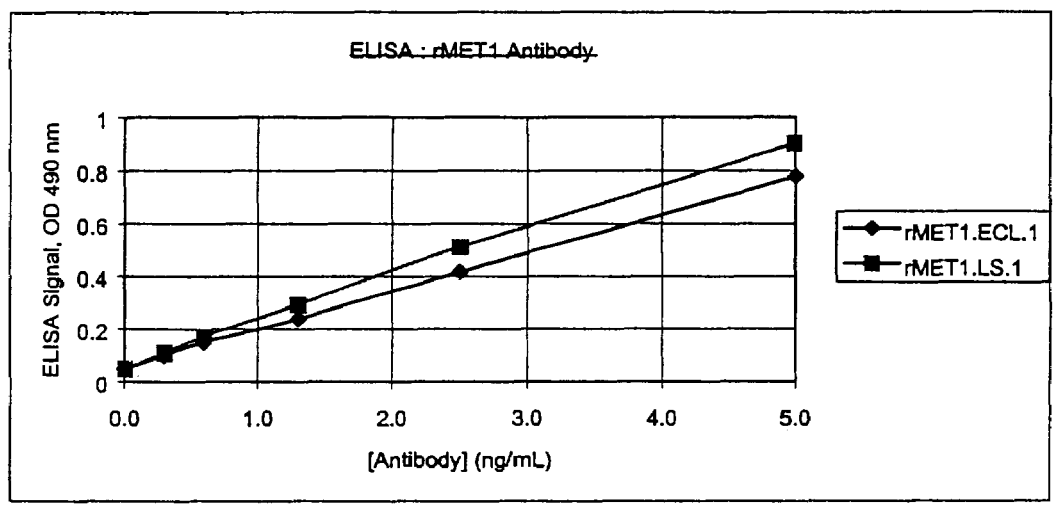
FIG. 2 shows expression of rMET1 antibody in *E. coli* with different eukaryotic signal sequences on the heavy and light chains.

Replicate 500 mL shake flask cultures for these two clones were induced with different concentrations of L-rhamnose, and then purified and analyzed as described in Example 6. The purified antibody yields are tabulated for comparison in Table 6. For the antibodies produced at optimal L-rhamnose concentrations, the ELISA standard curves are plotted in FIG. 2.

TABLE 5

| [L-rhamnose] (g/L) | Antibody Yield (mg/500 mL Culture) | |
|---|---|---|
| | Clone rMET10.ECL.20 | Clone rMET10.LS.1 |
| 0 | 0.0 | 0.4 |
| 0.001 | 0.2 | — |
| 0.01 | 2.9 | — |
| 0.1 | 3.1 | — |
| 1.0 | 2.5 | 2.3 |
| 3.0 | — | 3.0 |
| 6.0 | — | 4.8 |
| 9.0 | — | 3.5 |

TABLE 6

| [L-rhamnose] (g/L) | Antibody Yield (mg/500 mL Culture) | |
|---|---|---|
| | Clone rMET1.ECL.1 | Clone rMET1.LS.1 |
| 0 | 0.1 | 0.1 |
| 0.001 | 0.5 | — |
| 0.01 | 0.4 | — |
| 0.1 | 0.3 | — |
| 1.0 | 0.5 | 1.1 |
| 3.0 | — | 2.6 |
| 6.0 | — | 2.6 |
| 9.0 | — | 1.4 |

Example 8

Construction of Display Vector having Eukaryotic Signal Sequences

Display vectors, including antibody phage display vectors as described herein, having eukaryotic signal sequences were constructed.

The antibody phage display vector for cloning antibodies was derived from the M13 vector BS51. BS51 is identical to BS45 described in Example 5 of U.S. Pat. No. 6,057,098, except the last codon of the pelB signal sequence in BS45 was removed in BS51 by oligonucleotide directed mutagenesis (Kunkel, Proc. Natl. Acad. Sci. U.S.A 82:488 (1985); Kunkel, et al., Methods. Enzymol. 154:367 (1987)).

The prokaryotic signal sequences on the kappa chain and heavy chain were deleted from BS51 by oligonucleotide directed mutagenesis. Oligonucleotide BB (Table 2) was used to delete the pelB signal sequence on the kappa chain and oligonucleotide CC (Table 2) was used to delete the alkaline phosphatase signal sequence on the heavy chain.

Deletion of both signal sequences was determined by amplifying the DNA sequence containing both constant regions by PCR using oligonucleotides M and KK (Table 2), and oligonucleotides M and LL (Table 2), followed by sizing the PCR products on DNA agarose gel. The PCR was accomplished as described in Example 3 of U.S. Pat. No. 6,057,098 for the double-stranded DNA, except 1 µL of phage was template instead of cDNA. Phage with the desired deletions did not have PCR product for either of the oligonucleotide combinations. The sequence of two clones having no PCR product by agarose gel electrophoresis was verified at Macconnell Research as described in Example 1 using oligonucleotide primers L and M (Table 2) that bind on the 3' side of the kappa chain and heavy chain respectively. Both clones had the correct sequence. Uracil template was made from one phage stock having both deletions, as described in Example 6 of U.S. Pat. No. 6,057,098. This template, BS55, was used to insert the eukaryotic signal sequences for the kappa chain and IgG1.

The eukaryotic signal sequences were inserted into BS55 by oligonucleotide directed mutagenesis. Oligonucleotide DD (Table 2) was used to insert signal sequence of SEQ ID NO:43 into the kappa chain, and oligonucleotide EE (Table 2) was used to insert signal sequence of SEQ ID NO:45 into the heavy chain. Insertion of both signal sequences was determined by amplifying the DNA sequence containing both constant regions by PCR using oligonucleotides 1 (Table 8) and H (Table 2), followed by sizing the PCR products on DNA agarose gel. The PCR was accomplished as described in Example 3 of U.S. Pat. No. 6,057,098 for the double-stranded DNA, except 3 µL of phage was template instead of cDNA. Phage with the desired insertion had a larger PCR product than BS55 control. The sequence of three clones having what appeared to be a double insertion by agarose gel electrophoresis was verified at MacConnell Research as described in Example 1 using oligonucleotide primers L and M (Table 2) that bind on the 3' side of the kappa chain and heavy chain, respectively. All three clones had the correct sequence. The uracil template having eukaryotic signal sequences, called BS60, was prepared as described in Example 6 of U.S. Pat. No. 6,057,098.

Example 9

Polypeptide Display and Selection

Display vectors, including antibody phage display vectors, having eukaryotic signal sequences were utilized for polypeptide display and selection.

Display and Selection of rMet1 in a Phage Display Vector Having Eukaryotic Signal Sequences The kappa chain and heavy chain ss-DNA variable region sequences were prepared for rMet1 generally as described in Example 3 and 4 of U.S. Pat. No. 6,057,098. Oligonucleotides 41 and 971 (Table 7) were used to amplify the kappa chain variable region and oligonucleotides 204 and 1170 (Table 8) were used to amplify the heavy chain variable region. The single stranded DNA reactions (4×100 μL each) were done using only oligonucleotide 1 for the heavy chain and oligonucleotide 2 for the kappa chain (Tables 7 and 8). The single stranded DNA was purified and combined into BS60 uracil template as described in Example 7 of U.S. Pat. No. 6,057,098 except only a 250 μg scale of uracil template was used. The annealing was accomplished by incubating the sample at 70° C. for 2 min and slow cooling to less than 37° C. After the extension and ligation, 90 μL of mutagenesis stop buffer was added to the mixture and 1 μL of diluted DNA was electroporated into 40 μL *E. coli* DH12S electrocompetent cells (Invitrogen, Carlsbad, Calif.) as described in Example 8 U.S. Pat. No. 6,057,098. Aliquots of the electroporated cells were plated on 100 mm plates. The plaques on the plates were overlayed with nitrocellulose filters, and the filters were developed with AP-methamphetamine as described in Example 13 of U.S. Pat. No. 6,057,098. Functional positive plaques were picked into 50 μL 2×YT.

TABLE 7

| Oligo# | Murine 5' Kappa Chain Specific PCR Primer Set 5' to 3' Sequence (SEQ ID NOS: 48-76) |
|---|---|
| 96 | CTC TGT TCT ACT CCA GCT TGG GCA GAT GTT TTG ATG ACC CAA ACT CC |
| 97 | CTC TGT TCT ACT CCA GCT TGG GCA GAC ATC CAG ATG ACC CAG TCT CC |
| 98 | CTC TGT TCT ACT CCA GCT TGG GCA GAT ATC CAG ATG ACA CAG ACT AC |
| 99 | CTC TGT TCT ACT CCA GCT TGG GCA GAC ATT GTG ATG ACC CAG TCT CC |
| 128 | CTC TGT TCT ACT CCA GCT TGG GCA AAC ATT GTG CTG ACC CAA TCT CC |
| 129 | CTC TGT TCT ACT CCA GCT TGG GCA GAT GTT GTG ATG ACC CAA ACT CC |
| 189 | CTC TGT TCT ACT CCA GCT TGG GCA GAA ATT GTG CTC ACC CAG TCT CC |
| 190 | CTC TGT TCT ACT CCA GCT TGG GCA AGT ATT GTG ATG ACC CAG ACT CC |
| 13 | CTC TGT TCT ACT CCA GCT TGG GCA GAT ATT GTG CTA ACT CAG TCT CC |
| 17 | CTC TGT TCT ACT CCA GCT TGG GCA CAA ATT GTT CTC ACC CAG TCT CC |
| 38 | CTC TGT TCT ACT CCA GCT TGG GCA GAC ATT CAG CTG ACC CAG TCT CC |
| 39 | CTC TGT TCT ACT CCA GCT TGG GCA GAT ATT GTG ATG ACC CAG GCT GC |
| 40 | CTC TGT TCT ACT CCA GCT TGG GCA GAC CTT GTG CTG ACA CAG TCT CC |
| 41 | CTC TGT TCT ACT CCA GCT TGG GCA GAA AAT GTG CTC ACC CAG TCT CC |
| 42 | CTC TGT TCT ACT CCA GCT TGG GCA GAA ACA ACT GTG ACC CAG TCT CC |
| 43 | CTC TGT TCT ACT CCA GCT TGG GCA GAT GCT GTG ATG ACC CAG ATT CC |
| 44 | CTC TGT TCT ACT CCA GCT TGG GCA GAC ATC TTG CTG ACT CAG TCT CC |
| 45 | CTC TGT TCT ACT CCA GCT TGG GCA GAT GTT GTG ATA ACT CAG GAT GA |
| 46 | CTC TGT TCT ACT CCA GCT TGG GCA GAT GTT GTG GTG ACT CAA ACT CC |
| 47 | CTC TGT TCT ACT CCA GCT TGG GCA AAC ATT GTG ATG GCC TGG TCT CC |
| 54 | CTC TGT TCT ACT CCA GCT TGG GCA TCA TTA TTG CAG GTG CTT GTG GG |
| 55 | CTC TGT TCT ACT CCA GCT TGG GCA GAT ATT GTG ATA ACC CAG GAT GA |
| 56 | CTC TGT TCT ACT CCA GCT TGG GCA GAC ATT GTG ATG ACC CAG TCT CA |
| 57 | CTC TGT TCT ACT CCA GCT TGG GCA GAA ATG GTT CTC ACC CAG TCT CC |
| 58 | CTC TGT TCT ACT CCA GCT TGG GCA GAT GTT GTG CTG ACC CAA ACT CC |
| 59 | CTC TGT TCT ACT CCA GCT TGG GCA GAC GTT GTG ATG TCA CAG TCT CC |

TABLE 7-continued

| Oligo# | |
|---|---|
| 60 | CTC TGT TCT ACT CCA GCT TGG GCA GAC ATT GTG ACG TCA CAG TCT CC |
| 61 | CTC TGT TCT ACT CCA GCT TGG GCA CAA GTT GTT CTC ACC CAG TCT CC |
| 62 | CTC TGT TCT ACT CCA GCT TGG GCA GAC GTC CAG ATA ACC CAG TCT CC |
| | Murine 3' Kappa Chain Specific PCR Primers 5' to 3' Sequence (SEQ ID NOS: 77-78) |
| 2 | AC AGT TGG TGC AGC ATC AGC |
| 971 | GAA GCA CAC GAC TGA GGC ACC |

TABLE 8

| Oligo# | |
|---|---|
| | Murine 5' Heavy Chain Specific PCR Primer Set 5' to 3' Sequence (SEQ ID NOS: 79-111) |
| 185 | GTT GCA CTG CAG GCT CAA GCG GAG GTG CAG CTT CAG GAG TCA GG |
| 186 | GTT GCA CTG CAG GCT CAA GCG CAG GTC CAG CTG CAG CAG TCT GG |
| 188 | GTT GCA CTG CAG GCT CAA GCG GAA GTG CAG CTG GTG GAG TCT GG |
| 187 | GTT GCA CTG CAG GCT CAA GCG GAG GTG AAG CTG GTG GAA TCT GG |
| 18 | GTT GCA CTG CAG GCT CAA GCG CAG GTG CAG CTG AAG GAG TCA GG |
| 19 | GTT GCA CTG CAG GCT CAA GCG CAG GTT ACG CTG AAA GAG TCT GG |
| 48 | GTT GCA CTG CAG GCT CAA GCG GAG GTG AAG CTG GAT GAG ACT GG |
| 49 | GTT GCA CTG CAG GCT CAA GCG GAG GTA AAG CTT CTC GAG TCT GG |
| 50 | GTT GCA CTG CAG GCT CAA GCG GAA ATG AGA CTG GTG GAA TCT GG |
| 53 | GTT GCA CTG CAG GCT CAA GCG GAA GTG AAG CTG GTG GAG TCT GA |
| 64 | GTT GCA CTG CAG GCT CAA GCG CAG GTT CAG CTG CAA CAG TCT GA |
| 66 | GTT GCA CTG CAG GCT CAA GCG GAG ATC CAG CTG CAG CAG TCT GG |
| 67 | GTT GCA CTG CAG GCT CAA GCG GAA GTG ATG CTG GTG GAG TCT GG |
| 68 | GTT GCA CTG CAG GCT CAA GCG GAG GTG CAG CCT GTT GAG TCT GG |
| 69 | GTT GCA CTG CAG GCT CAA GCG GAC GTG AAG CAT ATG GAG TCT GG |
| 70 | GTT GCA CTG CAG GCT CAA GCG GAA GTG AAG CTT GAG GAG TCT GG |
| 71 | GTT GCA CTG CAG GCT CAA GCG GAG GTC CAG CTT CAG CAG TCA GG |
| 73 | GTT GCA CTG CAG GCT CAA GCG CAG GTC CAG CTG CAG CAG TCT AG |
| 74 | GTT GCA CTG CAG GCT CAA GCG CAG GTC CAG CTG CAG CAG TCT CG |
| 75 | GTT GCA CTG CAG GCT CAA GCG GAG GTT CAG CTG CAG CAG TCT GT |
| 124 | GTT GCA CTG CAG GCT CAA GCG CAG GTC CAA CTG CAG CAG CCT GG |
| 125 | GTT GCA CTG CAG GCT CAA GCG GAG GTT CAG CTG CAG CAG TCT GG |
| 126 | GTT GCA CTG CAG GCT CAA GCG GAG GTC CAG CTG CAA CAA TCT GG |
| 127 | GTT GCA CTG CAG GCT CAA GCG CAG GTC CAC GTG AAG CAG TCT GG |
| 204 | GTT GCA CTG CAG GCT CAA GCG GAT GTG CAG CTT CAG GAG TCG GG |
| 205 | GTT GCA CTG CAG GCT CAA GCG CAA GTT ACT CTA AAA GAG TCT GG |
| 207 | GTT GCA CTG CAG GCT CAA GCG GAA GTG CAG CTG TTG GAG ACT GG |

TABLE 8-continued

| Oligo# | |
|---|---|
| 51 | GTT GCA CTG CAG GCT CAA GCG CAG ATC CAG TTG GTG CAA TCT GG |
| 63 | GTT GCA CTG CAG GCT CAA GCG GAT GTG AAC TTG GAA GTG TCT GG |
| 72 | GTT GCA CTG CAG GCT CAA GCG CAG GCT TAT CTA CAG CAG TCT GG |
| 206 | GTT GCA CTG CAG GCT CAA GCG CAG GTC CAA GTG CAG CAG CCT GG |
| 208 | GTT GCA CTG CAG GCT CAA GCG GAA GTG CAG CTG GTG GAG ACT GC |
| 526 | GTT GCA CTG CAG GCT CAA GCG GAC GTG CAG GTG GTG GAG TCT GG |
| | Murine Heavy Chain Specific 3' PCR Primers 5' to 3' Sequence (SEQ ID NOS: 112-113) |
| 1 | GAT GGG GGT GTC GTT TTG GC |
| 1170 | CTG GAC AGG GAT CCA GAG TTC |

A functional positive plaque from a plaque lift of rMET1 mutagenesis was chosen for display of the antibody on the surface of M13. A plaque was picked off a plate into 50 µL 2YT. The tube was vortexed, then 40 µL of the phage was plated on a 150 mm LB agar plate as described in Example 12 of U.S. Pat. No. 6,057,098. The plate was incubated at 37° C. for 4 hr, then overnight at 20° C. The antibody phage was eluted off the plate as described in Example 15 of U.S. Pat. No. 6,057,098. The phage was set up for panning by diluting 200 µL phage into 2 mL panning buffer (40 mM TRIS, 150 mM NaCl, 20 mg/mL BSA, 0.25% casein, 0.1% Tween20 (Fisher Scientific, Pittsburgh, Pa.), pH 7.5) and aliquoting the phage into 2×1 mL fractions. Added 10 µL $10^{-6}$M reduced methamphetamine BSA-biotin (Example 4) to one of the fractions and nothing to the second fraction. Samples were incubated for 1 hr at room temperature to achieve equilibrium between antibody and antigen. The phage samples were then panned with avidin magnetic latex (Bangs Laboratories, Fishers, Ind.) generally as described in Example 14 of U.S. Pat. No. 6,057,098 with the following differences. All of the liquid handling steps were performed on a Tecan Genesis 150 robot (Tecan, Charlotte, N.C.) according to the manufacturers' recommendations. After the avidin latex was incubated with the phage for 10 min, the tubes were placed on the magnet to separate the latex without diluting the phage with panning buffer. The avidin latex was washed 3 times with 1 mL panning buffer each. The avidin latex was resuspended in 500 µL 2YT after the final wash. Aliquots of the latex from the foreground sample and the background sample were plated on 100 mm LB agar plates (Example 12 of U.S. Pat. No. 6,057,098). The plaques were counted to get a foreground to background ratio of 617:1, indicating that the antibody is displayed very well on the M13 phage.

One of the functional positive plaque picks was subcloned into pBRsaCH3 (Example 1) generally as described in Example 18 of U.S. Pat. No. 6,057,098. When subcloning this monoclonal, oligonucleotides W (Table 2) and 1 (Table 8) were used to amplify the kappa chain and the variable region of the heavy chain, and oligonucleotides R and MM (Table 2) were used to amplify the heavy chain constant region. For each PCR reaction, 3 µL of phage was used as template. The two PCR products and the pBRsaCH3 vector (cut with Sac I and HindIII) were all digested with T4 DNA polymerase, annealed and electroporated as described in Example 18 of U.S. Pat. No. 6,057,098. Three rMet1 clones were sequenced at MacConnell Research as described in Example 1 using oligonucleotide primers K and N (Table 2), that bind on the 5' side of the kappa chain and 3' side of the heavy chain, respectively.

Example 10

Polyclonal Phase Enrichment

Polyclonal phage having eukaryotic signal sequences for polypeptide expression and display were enriched, including by panning methods as described herein.

Polyclonal Phage Enrichment of Polyclonal Phage to Matrix Metalloproteinase 9 Precursor (Pro-MMP9) having Eukaryotic Signal Sequences The first round antibody phage generally was prepared as described in Example 7 of U.S. Pat. No. 6,057,098 using BS60 uracil template (Example 8) with the following differences. The oligonucleotides used to make the double-stranded PCR products as described in Example 3 of U.S. Pat. No. 6,057,098 are shown in Tables 7 and 8. A separate preparation of complementary cDNA (Example 2 of U.S. Pat. No. 6,057,098) was not made. Instead, Superscript One Step RT-PCR with Platinum Taq (Invitrogen, Carlsbad, Calif.) was used according to the manufacturers' recommendations to amplify DNA starting with RNA template. The HPLC gradient (Example 4 of U.S. Pat. No. 6,057,098) that separates the single stranded DNA from the double stranded DNA was shortened. The annealing of the uracil template and the ss-DNA inserts was done using the following thermal profile: 2 min 30 sec at 70° C., 70° C. to 42° C. ramp over 10 min, hold at 42° C. 10 sec, store at 4° C. The mutagenesis DNA was purified using QIAquick PCR Purification columns (Qiagen, Valencia, Calif.) according to the manufacturers' specifications. The mutagenesis DNA was eluted from the columns in 30 µL of elution buffer and 1 µL was electroportated into 40 µL DH12S electrocompetent cells. The electroporated cells were resuspended in 1 mL mixture of overnight XL1 cells (0.6 mL) and 2YT (0.4 mL). The entire 1 mL sample was plated on a 150 mm LB agar plate. The plate was incubated at 37° C. for 4 hr, followed by overnight incubation at 20° C. The first round antibody phage samples were eluted from the plates as described in Example 15 of U.S. Pat. No. 6,057,098.

Four electroporations of mutagenesis DNA were done from 2 different spleens (2 electroporations from each spleen) yielding 4 different phage samples. Panning with pro-MMP9- biotin was set up for each sample by mixing 950 µL first round phage, 50 µL 1M Tris, pH 8, 30 µL 300 mg/mL BSA, 50 µL 5% casein (Hammersten grade, Research Organics, Cleveland, Ohio) and 1 µL $10^{-7}$ M pro-MMP9-biotin (Example 4) and incubating 3 hr at room temperature.

The antibody phage samples were panned with avidin magnetic latex as described in Example 9 with rMET1 antibody phage. After the last wash, each latex was resuspended in 500 µL 2×YT, then the entire latex of each sample was plated on 150 mm LB plates to generate the 2nd round antibody phage. The 150 mm plates were incubated at 37° C. for 4 hr, then overnight at 20° C.

The resulting $2^{nd}$ round antibody phage samples were enriched for polyvalent display using the decapeptide tag on the kappa chain and the 7F11 magnetic latex generally as described in Example 16 of U.S. Pat. No. 6,057,098. All of the liquid handling steps were performed on a Tecan Genesis 150 robot according to the manufacturers recommendations. Panning with pro-MMP9-biotin was set up for each sample by mixing 1 mL 7F11/decapeptide enriched phage, and 5 µL $1.49\times10^{-6}$ M pro-MMP9-biotin and incubating 1.5 hr at room temperature. The phage samples were then panned with avidin magnetic latex and plated on LB agar plates as described above for round 1 antibody phage.

The resulting $3^{rd}$ round antibody phage samples were enriched for polyvalent display using the decapeptide tag on the kappa chain and the 7F11 magnetic latex, then panned with avidin magnetic latex as described above for the $2^{nd}$ round antibody phage samples.

The $4^{th}$ round antibody phage samples were pooled by mixing 150 µL of each $4^{th}$ round phage stock. The pooled antibody phage was set up in duplicate for a $4^{th}$ round of functional panning as described above using 900 µL panning buffer, 100 µL $4^{th}$ round pooled-antibody phage. One sample (foreground) received 10 µL $10^{-7}$M pro-MMP9-biotin and the other sample (background) did not receive pro-MMP9-biotin and served as a blank to monitor non-specific binding of phage to the magnetic latex. After overnight incubation at 2-8° C., the phage samples were panned with avidin magnetic latex as described above. The next day, the $5^{th}$ round antibody phage was eluted and the number of plaques was counted on the foreground and background plates. The foreground:background ratio was 2.1:1.

The $5^{th}$ round antibody phage was set up in duplicate as described above for the $4^{th}$ round phage except added 6.7 µL $1.49\times10^{-6}$ M pro-MMP9-biotin to the foreground sample. After 1 hour at room temperature, the phage samples were panned with avidin magnetic latex and processed as described above. The $6^{th}$ round antibody phage sample had a foreground:background ratio 21.8:1. These results indicate that a diverse library of antibodies was displayed on phage and high affinity antibodies selected.

Example 11

Cloning, Expression, Purification and Modifications of Polypeptides

Polypeptides, including polypeptides useful as immunogens for antibody production as described herein, were cloned, expressed, purified and modified.

Cloning, Expression, Purification and Biotinylation of Human Matrix Metalloproteinase-9 Precursor (Pro-MMP9)

The immunogen used for antibody production was prepared by Biosite Incorporated. PCR primers were made corresponding to sequence at the 5'-end of human pro-MMP9 and the coding sequence at the 3'-end of human pro-MMP9 (Genbank accession number J05070), including six histidine codons inserted between the end of the coding sequence and the stop codon to assist in purification of the recombinant protein by metal-chelate affinity chromatography, primers FF and GG, respectively (Table 2). The 5' primer also contains 21 base pairs of pEAK12 vector sequence (Edge BioSystems, Gaithersburg, Md.) at its 5'-end corresponding to the EcoRI site and sequence immediately upstream. The 3' primer contains approximately 20 nucleotides of vector sequence, including 6 bases of the NotI site and the sequence immediately downstream, at its 5' end. The vector sequence at the 5'-ends of these primers will form, upon treatment with T4 DNA polymerase, single-stranded overhangs that are specific and complementary to those on the pEAK12 vector. The PCR amplification of the pro-MMP9 gene insert was done on a 2×100 µl reaction scale containing 100 pmol of 5' primer (FF), 100 pmol of 3' primer (GG), 2.5 units of Expand polymerase, 10 µl 2 mM dNTPs, 10 µl 10x Expand reaction buffer, 1 µl of Clontech Quick-clone human spleen cDNA (Clontech Laboratories, Palo Alto, Calif.) as template, and water to 100 µl. The reaction was carried out in a Perkin-Elmer thermal cycler as described in Example 18 (U.S. Pat. No. 6,057,098). The PCR products were precipitated and fractionated by agarose gel electrophoresis and full-length products excised from the gel, purified, and resuspended in water (Example 17, U.S. Pat. No. 6,057,098). The pEAK12 vector was prepared to receive insert by digestion with NotI and EcoRI (New England BioLabs, Beverly, Mass.). The insert and EcoRI/NotI digested pEAK12 vector were prepared for T4 exonuclease digestion by adding 1.0 µl of 10x Buffer A to 1.0 µg of DNA and bringing the final volume to 9 µl with water. The samples were digested for 4 minutes at 30° C. with 1 µl (1U/µl) of T4 DNA polymerase. The T4 DNA polymerase was heat inactivated by incubation at 70° C. for 10 minutes. The samples were cooled, briefly centrifuged, and 45 ng of the digested insert added to 100 ng of digested pEAK12 vector in a fresh microfuge tube. After the addition of 1.0 µl of 10x annealing buffer, the volume was brought to 10 µl with water. The mixture was heated to 70° C. for 2 minutes and cooled over 20 minutes to room temperature, allowing the insert and vector to anneal. The annealed DNA was diluted one to four with distilled water and electroporated (Example 8, U.S. Pat. No. 6,057,098) into 30 µl of electrocompetent *E. coli* strain, DH10B (Invitrogen, Carlsbad, Calif.). The transformed cells were diluted to 1.0 ml with 2×YT broth and 10 µl, 100 µl, 300p plated on LB agar plates supplemented with ampicillin (75 µg/ml) and grown overnight at 37° C. Colonies were picked and grown overnight in 2×YT (75 µg/ml ampicillin at 37° C. The following day glycerol stocks were made for long term storage at −80° C. The sequence of these clones (pro-MMP9peak12) was verified at MacConnell Research as described in Example 1 using oligonucleotide primers HH and II (Table 2) that bind on the 5' and 3' side of the insert in the pEAK12 vector, respectively. Plasmid suitable for transfection and the subsequent expression and purification of human pro-MMP9 was prepared from clone pro-MMP9peak12 using an EndoFree Plasmid Mega Kit as per manufacturers' recommendations (Qiagen, Valencia, Calif.).

HEK 293 ("Peak") cells were expanded into a T-75 flask from a 1 ml frozen vial stock ($5\times10^6$ cells/ml) in IS 293 medium (Irvine Scientific, Santa Ana, Calif.) with 5% fetal bovine serum (FBS) (JRH Biosciences, Lenexa, Kans.), 20 units/ml Heparin, 0.1% Pluronic F-68 (JRH Biosciences, Lenexa, Kans.), and 50 µg/ml Gentamicin (Sigma, St. Louis, Mo.). After incubating at 37° C., 85% humidity, and 5% $CO_2$ for 2-3 days, the cells were expanded into a T-175 flask while reducing the FBS to 2% in the medium. The cells were then continuously expanded 1:2 over a period of 2-3 weeks, establishing a consistent mono-layer of attached cells. Peak cells grown with the above method were centrifuged at 1000 rpm for 6 minutes, and the supernatant was discarded. After counting the cells to establish the density and checking for at least 90% viability with a standard dye test, the cells were resuspended at $5 \times 10^5$ cells/ml in 400 ml IS 293 with 2% FBS and 50 µg/ml Gentamicin and added to a 1 L spinner flask. Then, to a conical tube 5 ml IS 293 and 320 ug pro-MMP9 DNA were added per 400 ml spinner flask. This was mixed and incubated at room temperature for 2 minutes. X-tremeGENE RO-1539 transfection, 400 ul, (Roche Diagnostics, Indianapolis, Ind.) per spinner was added to the tube that was then mixed and incubated at room temperature for 20 minutes. The mixture was added to the spinner flask, and incubated at 37° C., 85% humidity, and 5% $CO_2$ for 4 days at 100 rpm. The cell broth from the above spinner flask was spun down at 3500 rpm for 20 minutes, and the supernatant was saved for purification of the pro-MMP9. A column containing 20 ml Chelating Fast Flow resin (Amersham Pharmacia Biotech, Piscataway, N.J.) charged with $NiCl_2$ was equilibrated with BBS (20 mM borate, 150 mM NaCl, 0.01% $NaN_3$). Then the supernatant from the spinner flask was loaded on the column, washed with BBS, 10 mM imidazole, and eluted with BBS, 200 mM imidazole. The elution was used for the load of the next purification step after adding $CaCl_2$ to 10 mM. A column with 5 ml gelatin sepharose 4B resin (Amersham Pharmacia Biotech, Piscataway, N.J.) was equilibrated with a BBS, 10 mM $CaCl_2$ buffer. After loading the antigen, the column was washed with equilibration buffer, and the pro-MMP9 was eluted with a BBS, 10 mM $CaCl_2$, 2% dimethyl sulfoxide (DMSO) (Sigma, St. Louis, Mo.) buffer. Polyoxyethyleneglycol dodecyl ether (BRIJ-35) (0.005%) and EDTA (10 mM) were added to the elution, which was then dialyzed into the final buffer (50 mM Tris, 400 mM NaCl, 10 mM $CaCl_2$, 0.01% $NaN_3$, pH 7.5, 0.005% BRIJ-35, 10 mM EDTA). Finally, the protein was concentrated to approximately 0.25 mg/ml for storage at 4° C. Zymogram gels were used to check for production and purification of pro-MMP9. Western blots were also used to check for activity of the protein. Pro-MMP9 (Oncogene Research Products, Cambridge, Mass.) was used for comparison of the purified antigen made using the PEAK cell system to known standards. Pro-MMP9 was biotinylated as described in Example 9 of U.S. Pat. No. 6,057,098.

Example 12

Cloning of Polypeptide Antigens Using Eukaryotic Signal Sequences

Polypeptide antigens were cloned and expressed using eukaryotic signal sequences, including using a human ceruloplasmin signal sequence as described herein.

Cloning of the Mature Macaque Interleukin-8 Antigen using a Human Ceruloplasmin Signal Sequence PCR primers were made corresponding to the coding sequence at the 5'-end of the mature macaque interleukin-8 antigen and the coding sequence at the 3'-end of macaque interleukin-8, primers Y and Z, respectively (Table 2). Specifically, the 5' primer contains 22 base pairs of vector sequence at its 5'-end corresponding to the 3'-end of the pBRsaCH3 vector, seven histidine codons, and an enterokinase cleavage site upstream of the coding sequence. The 3' primer contains the 19 nucleotides of tet promoter removed by HindIII digestion, in addition to 24 nucleotides of vector sequence 3' to the HindIII site at its 5' end (Example 17, U.S. Pat. No. 6,057,098).

The PCR amplification of the interleukin-8 gene insert was done on a 3×100 µl reaction scale each containing 100 µmol of 5' primer Y, 100 µmol of 3' primer Z, 2 units of Expand polymerase, 10 µp 2 mM dNTPs, 10 µp 10x Expand reaction buffer, 50 ng of a human IL-8 plasmid preparation as template and water to 100 µl. The human IL-8 plasmid was prepared from an overnight culture of a human IL-8 clone using a Qiagen High-Speed Plasmid Midi Kit following manufacturers' recommendations. This IL-8 clone came from process described in PCT Application 98/06704. The reaction was carried out in a Perkin-Elmer thermal cycler (Model 9600) using the following thermal profile: one cycle of denaturation at 94° C. (1 min); ten cycles of denaturation (15 sec, 94° C.), annealing (30 sec, 55 elongation (60 sec, 72° C.); twenty cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The PCR products were precipitated and fractionated by agarose gel electrophoresis and full-length products excised from the gel, and purified with a Qiagen HiSpeed Plasmid Purification Midi Kit. The concentration of the insert was determined by $A_{260}$. The insert and SacI/HindIII digested pBRsaCH3 vector (Example 1) were prepared for T4 exonuclease digestion by adding 1.0 µl of 10x Buffer A to 1.0 µg of DNA and bringing the final volume to 9 µl with water. The samples were digested for 4 minutes at 30° C. with 1 µl (1U/µl) of T4 DNA polymerase. The T4 DNA polymerase was heat inactivated by incubation at 70° C. for 10 minutes. The samples were cooled, briefly spun, and 80 ng of the digested insert added to 100 ng of digested pBRsaCH3 vector in a fresh microfuge tube. After the addition of 1.0 µl of 10x annealing buffer, the volume was brought to 10 µl with water and the mixture heated to 70° C. for 2 minutes and cooled over 20 minutes to room temperature to allow the insert and vector to anneal. After annealing, the insert and vector were ligated together by adding 1.0 µl of 10 x synthesis buffer, 1.0 µl T4 DNA ligase (1U/µl), 1.0 µl diluted T7 DNA polymerase (1U/µl) and incubating at 37° C. for 30 min. The annealed DNA was diluted one to three with distilled water and 1 µl electroporated (Example 8, U.S. Pat. No. 6,057,098) into 40 µl of electrocompetent *E. coli* strain, DH10B. The transformed cells were diluted to 1.0 ml with 2×YT broth and 1.0 µl, 50 µl, 200 µl plated on LB agar plates supplemented with tetracycline (10 µg/ml) and grown overnight at 37° C. Colonies were picked and grown overnight in 50 ml 2×YT (20 µg/ml tetracycline) at 37° C. The following day glycerol freezer stocks were made for long term storage at −80° C. and plasmid purified from the remaining overnight culture using a QiaPrep column (Qiagen, Valencia, Calif.). The sequence of three clones was verified at MacConnell Research as described in Example 1 using oligonucleotide primer N (Table 2) that binds on 3' side of the insert in the pBRsaCH3 vector. All three clones, mac-il8-5'his.1, mac-il8-5'his.2, and mac-il8-5'his.3 had the correct sequence. The macaque interleukin-8 antigen was expressed and purified by nickel-chelate chromatography as described in Example 13.

Example 13

Expression and Purification of Polypeptides

Polypeptides, including polypeptide antigens as described herein, were expressed and purified.

Expression and Purification of Macaque IL-8 Antigen

This clone consisted of host *E. coli* strain DH10B rha+ electroporated with a plasmid expressing macaque IL-8 antigen as described in Example 12. This construct had a septahistidine tag, an enterokinase cleavage site, and human ceruloplasmin signal sequence, in that order, engineered on the N-terminus. The cells were cultured under 10 µg/mL tetracycline selection.

Ten replicate 500 mL shake flask cultures were each induced with 4 g/L of L-rhamnose and purified through Chelating Sepharose FF chromatography as described in Example 3. The elutions were pooled and buffer exchanged into 50 mM Tris, 0.01% $NaN_3$, pH 8 buffer. The protein solution was then supplemented with enterokinase (Roche Diagnostics, Indianapolis, Ind.) to 6 µg/mL and incubated overnight at 4° C. to cleave the septahistidine tag on the macaque IL-8 antigen.

Next, the digested protein solution was buffer exchanged into 10 mM $NaPO_4$, 40 mM NaCl, 0.01% $NaN_3$, pH 7.4 buffer and passed through a disposable chromatography column packed with 5 mL of Q Sepharose FF resin and equilibrated in the same buffer. Several contaminants from the first purification step bound to the column, while the flow through contained the macaque IL-8 antigen.

The Q Sepharose flow through was supplemented with imidazole to 10 mM imidazole and passed through a disposable chromatography column packed with 5 mL of Chelating Sepharose FF resin charged with 0.1 M $NiCl_2$ and equilibrated in 20 mM borate, 150 mM NaCl, 10 mM imidazole, 0.01% $NaN_3$, pH 8.0 buffer. In this step, the flow through contained the macaque IL-8 antigen since it no longer contained the N-terminal septahistidine tag, and a sole remaining contaminant was bound to the column.

The Chelating Sepharose FF flow through was then processed with YM-10 Centriprep centrifugal concentrators (Millipore, Bedford, Mass.), following which, the concentrate was buffer exchanged into 50 mM $NaPO_4$, 150 mM NaCl, pH 7 buffer. This was passed through a disposable chromatography column packed with 2.5 mL of High Q resin (Bio-Rad, Hercules, Calif.) equilibrated in the same buffer. In this step, endotoxin was bound to the column, while the flow through contained macaque IL-8 antigen. The purified macaque IL-8 antigen was subjected to terminal 0.2 µm syringe filtration and stored at 4° C. The final yield was 1.9 mg of macaque IL-8 antigen.

The concentration of the purified macaque IL-8 antigen was measured by absorbance at 280 nm with an extinction coefficient of 0.7 (mL)/(mgcm). The purified antigen was analyzed by SDS-PAGE using a 4-20% Tris-glycine gel (Invitrogen), and determined to have greater than 95% purity. The macaque Il-8 antigen and human IL-8 antigen (PCT Application 98/06704) were subjected to Western transfer onto an Immun-Blot™ PVDF membrane (Bio-Rad, Hercules, Calif.). The human IL-8 makes for a good control due to the high percent identity between macaque and human IL-8. Recombinant anti-human IL-8 Omniclonal™ antibodies MED002.1 and MED002A.2 (PCT Application 98/06704) were used for labeling, and goat anti-(human kappa)-alkaline phosphatase (Southern Biotechnology Associates) was used for secondary labeling and detection. The bands for both antigens were of comparable intensity on the Western blot.

---

What is claimed is:

1. A method of preparing a polypeptide display library, which method comprises the steps of introducing a polynucleotide encoding an exogenous polypeptide into the genome of a replicable genetic package to form a fusion protein with an endogenous protein that is normally expressed from the outersurface of the replicable genetic package, wherein the polynucleotide is operably linked to a eukaryotic signal sequence which encodes a signal peptide MGALAVFAVACLAAVASVAHA (SEQ ID NO: 3), and expressing said fusion protein, wherein the replicable genetic package is a bacteriophage or phagemid.

2. A method according to claim 1, wherein the polypeptide is a eukaryotic polypeptide.

3. A method according to claim 1, wherein the polypeptide is a prokaryotic polypeptide.

4. A method according to claim 1, wherein the polypeptide is an antibody.

5. A method according to claim 1, wherein the polypeptide is an antibody that is a mouse antibody, a human antibody, or a chimeric antibody.

6. A method according to claim 1, wherein the polypeptide is a whole antibody or binding fragment thereof.

7. A method according to claim 1, wherein the polypeptide is an antibody binding fragment that is a single chain fragment, an Fv fragment or a Fab fragment.

8. A method according to claim 1, wherein the signal sequence is 5' to the polynucleotide sequence encoding the polypeptide.

9. A method according to claim 1, wherein the signal sequence and the polypeptide are separated by zero amino acids.

10. A method according to claim 1, wherein the bacteriophage is a filamentous phage.

11. A method according to claim 10, wherein the filamentous phage is an M13, Fd, or F1 phage.

12. A method according to claim 1, further comprising the steps of (a) screening for the polypeptide, (b) enriching the polypeptide display library, and/or (c) subcloning the polynucleotide encoding the identified polypeptide into an expression vector.

* * * * *

SEQUENCE LISTING

<160> NUMBER OF SEQ ID NOS: 113

<210> SEQ ID NO 1
<211> LENGTH: 19
<212> TYPE: PRT
<213> ORGANISM: Homo sapiens
<220> FEATURE:
<223> OTHER INFORMATION: Human ceruloplasmin signal sequence

<400> SEQUENCE: 1

Met Lys Ile Leu Ile Leu Gly Ile Phe Leu Phe Leu Cys Ser Thr Pro
1               5                   10                  15

Ala Trp Ala

<210> SEQ ID NO 2
<211> LENGTH: 19
<212> TYPE: PRT
<213> ORGANISM: Homo sapiens
<220> FEATURE:
<223> OTHER INFORMATION: Human neutrophil defensin 1,2,3 precursor
      signal sequence

<400> SEQUENCE: 2

Met Arg Thr Leu Ala Ile Leu Ala Ala Ile Leu Leu Val Ala Leu Gln
1               5                   10                  15

Ala Gln Ala

-continued

<210> SEQ ID NO 3
<211> LENGTH: 21
<212> TYPE: PRT
<213> ORGANISM: Chlamydomonas reinhardtii
<220> FEATURE:
<223> OTHER INFORMATION: Arysulfatase precursor

<400> SEQUENCE: 3

Met Gly Ala Leu Ala Val Phe Ala Val Ala Cys Leu Ala Ala Val Ala
1               5                   10                  15

Ser Val Ala His Ala
            20

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Primer A

<400> SEQUENCE: 4
cgccaaggag acagtcataa tgaaatacct attgcctacg gc                          42

<210> SEQ ID NO 5
<211> LENGTH: 77
<212> TYPE: DNA
<213> ORGANISM: Artificial Sequence
<220> FEATURE:
<223> OTHER INFORMATION: Description of Artificial Sequence:Primer  B

<400> SEQUENCE: 5
gtgataaact accgcattaa agcttgcgtc atttacctac ttaagatcct caatgcatta      60
tgactgtctc cttggcg                                                     77

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer C

<400> SEQUENCE: 6
cctttcgtct tcaagaattc gtgagttagc tcactcatta gg                         42

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Primer D

<400> SEQUENCE: 7
ccctttcgtc ttcaagaatt cttaatcttt ctgcgaattg agatg                      45

<210> SEQ ID NO 8
<211> LENGTH: 79
<212> TYPE: DNA
<213> ORGANISM: Artificial Sequence
<220> FEATURE:
<223> OTHER INFORMATION: Description of Artificial Sequence: Primer E

<400> SEQUENCE: 8
gtgataaact accgcattaa agcttgcgtc atttacctac ttaagatcct caatgcataa      60
tgtgatcctg ctgaatttc                                                   79

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Primer F

<400> SEQUENCE: 9
gaaattcagc aggatcacat tatgaaatac ctattgccta cggc          44

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer G

<400> SEQUENCE: 10
atgtacaaag cgtgggtaac gc          22

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Primer H

<400> SEQUENCE: 11
actggtcgta atgaagccaa ggagacagtc ataatg          36

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer I

<400> SEQUENCE: 12
gcgtaggagt gtttatcgtc agc          23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer J

<400> SEQUENCE: 13
cacctgacgt ctaagaaacc          20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer K

<400> SEQUENCE: 14
cattttcctg tcagtaacga g          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer L

```
<400> SEQUENCE: 15
agtgccaagt gacgcgttct a                                              21

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Primer M

<400> SEQUENCE: 16
gcaactgttg ggaaggg                                                   17

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer N

<400> SEQUENCE: 17
gaggatgacg atgagcgc                                                  18

<210> SEQ ID NO 18
<211> LENGTH: 71
<212> TYPE: DNA
<213> ORGANISM: Artificial Sequence
<220> FEATURE:
<223> OTHER INFORMATION: Description of Artificial Sequence: Primer O

<400> SEQUENCE: 18
gtgataaact accgcattaa agcttatcga tgataagctg tcaattagtg atggtgatgg    60
tgatgagaat c                                                         71

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Primer P

<400> SEQUENCE: 19
ttctagaacg cgtcacttgg c                                              21

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence: Primer Q

<400> SEQUENCE: 20
gccaagtgac gcgttctaga attaagactc attcctgttg aagctctt                 48

<210> SEQ ID NO 21
<211> LENGTH: 74
<212> TYPE: DNA
<213> ORGANISM: Artificial Sequence
<220> FEATURE:
<223> OTHER INFORMATION: Description of Artificial Sequence: Primer R

<400> SEQUENCE: 21
gtgataaact accgcattaa agcttatcga tgataagctg tcaattagtg atggtgatgg    60
tgatgatgag aatc                                                      74
```

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: Primer S

<400> SEQUENCE: 22
gaaattcagc aggatcacat tatgaaaatc ctgattctcg gtatcttcct gtttctctgt     60
tctactccag cttgggcaga aaatgtgctc acccagtctg                          100

<210> SEQ ID NO 23
<211> LENGTH: 101
<212> TYPE: DNA
<213> ORGANISM: Artificial Sequence
<220> FEATURE:
<223> OTHER INFORMATION: Description of Artificial Sequence: Primer T

<400> SEQUENCE: 23
ctttgtacat ggagaaaata aaatgaagat tcttatcctg ggcatttttc ttttcctgtg     60
cagcacacca gcatgggctg atgtgcagct tcaggagtct c                        101

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Primer U

<400> SEQUENCE: 24
gtgataaact accgcattaa agcttctcat tcctgttgaa gctcttg                   47

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Primer V

<400> SEQUENCE: 25
gttgcactgc aggctcaagc ggatgtgcag cttcaggagt cggg                      44

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer W

<400> SEQUENCE: 26
ctctgttcta ctccagcttg ggca                                            24

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Primer X

<400> SEQUENCE: 27
ctctgttcta ctccagcttg ggcagaaaat gtgctcaccc agtctcc                   47

<210> SEQ ID NO 28
<211> LENGTH: 87

```
<212> TYPE: DNA
<213> ORGANISM: Artificial Sequence
<220> FEATURE:
<223> OTHER INFORMATION: Description of Artificial Sequence: Primer Y

<400> SEQUENCE: 28
ctctgttcta ctccagcttg ggcacaccat caccatcacc atcacgacga tgacgataaa    60
agtgctaaag aacttagatg tgagtgc                                        87

<210> SEQ ID NO 29
<211> LENGTH: 107
<212> TYPE: DNA
<213> ORGANISM: Artificial Sequence
<220> FEATURE:
<223> OTHER INFORMATION: Description of Artificial Sequence: Primer Z

<400> SEQUENCE: 29
gtgataaact accgcattaa agcttatcga tgataagctg tcaattatgg attttgattc    60
tcagccctct tcacaaactt ctccacaacc ctctgcaccc atggttc                  107

<210> SEQ ID NO 30
<211> LENGTH: 104
<212> TYPE: DNA
<213> ORGANISM: Artificial Sequence
<220> FEATURE:
<223> OTHER INFORMATION: Description of Artificial Sequence: Primer AA

<400> SEQUENCE: 30
gaaattcagc aggatcacat tatgaaaatc ctgattctcg gtatcttcct gtttctctgt    60
tctactccag cttgggagct cgaaaatgtg ctcacccagt ctcc                     104

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Primer BB

<400> SEQUENCE: 31
catcacgagc tcagtgtgcc agaggttgaa tatgactgcc tcc                      43

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Primer CC

<400> SEQUENCE: 32
aagctgcaca tccatgcaca gattccgttt attttctcca tg                       42

<210> SEQ ID NO 33
<211> LENGTH: 96
<212> TYPE: DNA
<213> ORGANISM: Artificial Sequence
<220> FEATURE:
<223> OTHER INFORMATION: Description of Artificial Sequence: Primer DD

<400> SEQUENCE: 33
gtctgggtca tcacgagctc ccaagctgga gtagaacaga gaaacaggaa gataccccga    60
gaatcaggat tttcattatg actgtctcct tggcgt                              96

<210> SEQ ID NO 34
<211> LENGTH: 101
```

```
<212> TYPE: DNA
<213> ORGANISM: Artificial Sequence
<220> FEATURE:
<223> OTHER INFORMATION: Description of Artificial Sequence: Primer EE

<400> SEQUENCE: 34
gactcctgaa gctgcacatc cgcttgagcc tgcagtgcaa caagcagaat agctgcaagg      60
atagccagag tacgcatttt attttctcca tgtacaaagc g                         101

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Primer FF

<400> SEQUENCE: 35
aggtgtcgta agcttgaatt cagacacctc tgccgccacc atgag                     45

<210> SEQ ID NO 36
<211> LENGTH: 63
<212> TYPE: DNA
<213> ORGANISM: Artificial Sequence
<220> FEATURE:
<223> OTHER INFORMATION: Description of Artificial Sequence: Primer GG

<400> SEQUENCE: 36
gggctggctt acctgcggcc ttagtgatgg tgatggtgat ggtcctcagg gcactgcagg     60
atg                                                                   63

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer HH

<400> SEQUENCE: 37
ttctcaagcc tcagacagtg                                                 20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Primer II

<400> SEQUENCE: 38
cctggatgca ggctactcta g                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Primer JJ

<400> SEQUENCE: 39
gcaactctct actgtttctc c                                               21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer KK
```

```
<400> SEQUENCE: 40
tcgctgccca accagccatg                                                   20

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Primer LL

<400> SEQUENCE: 41
acccgttttt ttggatggag tgaaacgatg aaacaaagca ctattgcact g                51

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer MM

<400> SEQUENCE: 42
gccaaaacga caccccatc                                                    20

<210> SEQ ID NO 43
<211> LENGTH: 57
<212> TYPE: DNA
<213> ORGANISM: Homo sapiens
<220> FEATURE:
<223> OTHER INFORMATION: Ceruloplasmin precursor signal sequence
<220> FEATURE:
<223> OTHER INFORMATION: Kappa chain

<400> SEQUENCE: 43
atgaaaatcc tgattctcgg tatcttcctg tttctctgtt ctactccagc ttgggca          57

<210> SEQ ID NO 44
<211> LENGTH: 57
<212> TYPE: DNA
<213> ORGANISM: Homo sapiens
<220> FEATURE:
<223> OTHER INFORMATION: Ceruloplasmin precursor
<220> FEATURE:
<223> OTHER INFORMATION: Heavy chain

<400> SEQUENCE: 44
atgaagattc ttatcctggg catttttctt ttcctgtgca gcacaccagc atgggct          57

<210> SEQ ID NO 45
<211> LENGTH: 57
<212> TYPE: DNA
<213> ORGANISM: Homo sapiens
<220> FEATURE:
<223> OTHER INFORMATION: Neutrophil defensin 1,2,3 signal sequence

<400> SEQUENCE: 45
atgcgtactc tggctatcct tgcagctatt ctgcttgttg cactgcaggc tcaagcg          57

<210> SEQ ID NO 46
<211> LENGTH: 63
<212> TYPE: DNA
<213> ORGANISM: Chlamydomonas reinhardtii
<220> FEATURE:
<223> OTHER INFORMATION: Arylsulfatase precursor

<400> SEQUENCE: 46
atgggtgctc tggcagtttt cgctgtagcg tgtctggcag ccgttgcgtc tgtagctcac       60
```

```
<210> SEQ ID NO 47
<211> LENGTH: 66
<212> TYPE: DNA
<213> ORGANISM: Artificial Sequence
<220> FEATURE:
<223> OTHER INFORMATION: Description of Artificial Sequence: Yeast
      Glycolipid Anchored Surface Protein Precursor
      Signal Sequence

<400> SEQUENCE: 47
atgctgttca aatctctctc caagctggct actgcagctg cgttctttgc aggtgttgct    60
actgct                                                               66

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific Primer 96

<400> SEQUENCE: 48
ctctgttcta ctccagcttg ggcagatgtt ttgatgaccc aaactcc                  47

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 97

<400> SEQUENCE: 49
ctctgttcta ctccagcttg ggcagacatc cagatgaccc agtctcc                  47

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specifc PCR Primer 98

<400> SEQUENCE: 50
ctctgttcta ctccagcttg ggcagatatc cagatgacac agactac                  47

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Murine 5'
      kappa Chain Specific PCR Primer 99

<400> SEQUENCE: 51
ctctgttcta ctccagcttg ggcagacatt gtgatgaccc agtctcc                  47

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 128
```

```
<400> SEQUENCE: 52
ctctgttcta ctccagcttg ggcaaacatt gtgctgaccc aatctcc          47

<210> SEQ ID NO 53
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 129

<400> SEQUENCE: 53
ctctgttcta ctccagcttg ggcagatgtt gtgatgaccc aaactcc          47

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 189

<400> SEQUENCE: 54
ctctgttcta ctccagcttg ggcagaaatt gtgctcaccc agtctcc          47

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 190

<400> SEQUENCE: 55
ctctgttcta ctccagcttg ggcaagtatt gtgatgaccc agactcc          47

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 13

<400> SEQUENCE: 56
ctctgttcta ctccagcttg ggcagatatt gtgctaactc agtctcc          47

<210> SEQ ID NO 57
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain SpecificPCR Primer 17

<400> SEQUENCE: 57
ctctgttcta ctccagcttg ggcacaaatt gttctcaccc agtctcc          47

<210> SEQ ID NO 58
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 38

<400> SEQUENCE: 58
```
ctctgttcta ctccagcttg ggcagacatt cagctgaccc agtctcc                     47

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 39

<400> SEQUENCE: 59
ctctgttcta ctccagcttg ggcagatatt gtgatgaccc aggctgc                     47

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 40

<400> SEQUENCE: 60
ctctgttcta ctccagcttg ggcagacctt gtgctgacac agtctcc                     47

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 41

<400> SEQUENCE: 61
ctctgttcta ctccagcttg ggcagaaaat gtgctcaccc agtctcc                     47

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 42

<400> SEQUENCE: 62
ctctgttcta ctccagcttg ggcagaaaca actgtgaccc agtctcc                     47

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 43

<400> SEQUENCE: 63
ctctgttcta ctccagcttg ggcagatgct gtgatgaccc agattcc                     47

<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 44

<400> SEQUENCE: 64
ctctgttcta ctccagcttg ggcagacatc ttgctgactc agtctcc                     47

<210> SEQ ID NO 65
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 45

<400> SEQUENCE: 65
ctctgttcta ctccagcttg ggcagatgtt gtgataactc aggatga            47

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 46

<400> SEQUENCE: 66
ctctgttcta ctccagcttg ggcagatgtt gtggtgactc aaactcc            47

<210> SEQ ID NO 67
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 47

<400> SEQUENCE: 67
ctctgttcta ctccagcttg ggcaaacatt gtgatggcct ggtctcc            47

<210> SEQ ID NO 68
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 54

<400> SEQUENCE: 68
ctctgttcta ctccagcttg ggcatcatta ttgcaggtgc ttgtggg            47

<210> SEQ ID NO 69
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 55

<400> SEQUENCE: 69
ctctgttcta ctccagcttg ggcagatatt gtgataaccc aggatga            47

<210> SEQ ID NO 70
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 56

<400> SEQUENCE: 70
ctctgttcta ctccagcttg ggcagacatt gtgatgaccc agtctca            47

<210> SEQ ID NO 71

```
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 57

<400> SEQUENCE: 71
ctctgttcta ctccagcttg ggcagaaatg ttctcaccc agtctcc                47

<210> SEQ ID NO 72
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 58

<400> SEQUENCE: 72
ctctgttcta ctccagcttg ggcagatgtt gtgctgaccc aaactcc                47

<210> SEQ ID NO 73
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 59

<400> SEQUENCE: 73
ctctgttcta ctccagcttg ggcagacgtt gtgatgtcac agtctcc                47

<210> SEQ ID NO 74
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 60

<400> SEQUENCE: 74
ctctgttcta ctccagcttg ggcagacatt gtgacgtcac agtctcc                47

<210> SEQ ID NO 75
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 61

<400> SEQUENCE: 75
ctctgttcta ctccagcttg ggcacaagtt gttctcaccc agtctcc                47

<210> SEQ ID NO 76
<211> LENGTH: 47
<212> TYPE: DNA
<213> ORGANISM: Artificial Sequence
<220> FEATURE:
<223> OTHER INFORMATION: Description of Artificial Sequence: Murine 5'
      Kappa Chain Specific PCR Primer 62

<400> SEQUENCE: 76
ctctgttcta ctccagcttg ggcagacgtc cagataaccc agtctcc                47

<210> SEQ ID NO 77
<211> LENGTH: 20
<212> TYPE: DNA
```

```
<213> ORGANISM: Artificial Sequence
<220> FEATURE:
<223> OTHER INFORMATION: Description of Artificial Sequence: Murine 3'
      Kappa Chain Specific PCR Primer 2

<400> SEQUENCE: 77
acagttggtg cagcatcagc                                                    20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Murine 3'
      Kappa Chain Specific PCR Primer 971

<400> SEQUENCE: 78
gaagcacacg actgaggcac c                                                  21

<210> SEQ ID NO 79
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 185

<400> SEQUENCE: 79
gttgcactgc aggctcaagc ggaggtgcag cttcaggagt cagg                         44

<210> SEQ ID NO 80
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 186

<400> SEQUENCE: 80
gttgcactgc aggctcaagc gcaggtccag ctgcagcagt ctgg                         44

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 188

<400> SEQUENCE: 81
gttgcactgc aggctcaagc ggaagtgcag ctggtggagt ctgg                         44

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 187

<400> SEQUENCE: 82
gttgcactgc aggctcaagc ggaggtgaag ctggtggaat ctgg                         44

<210> SEQ ID NO 83
<211> LENGTH: 44
<212> TYPE: DNA
<213> ORGANISM: Artificial Sequence
<220> FEATURE:
```

-continued

<223> OTHER INFORMATION: Description of Artificial Sequence: Murine 5'
      Heavy Chain Specific PCR Primer 18

<400> SEQUENCE: 83
gttgcactgc aggctcaagc gcaggtgcag ctgaaggagt cagg                44

<210> SEQ ID NO 84
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 19

<400> SEQUENCE: 84
gttgcactgc aggctcaagc gcaggttacg ctgaaagagt ctgg                44

<210> SEQ ID NO 85
<211> LENGTH: 44
<212> TYPE: DNA
<213> ORGANISM: Artificial Sequence
<220> FEATURE:
<223> OTHER INFORMATION: Description of Artificial Sequence: Murine 5'
      heavy Chain Specific PCR Primer 48

<400> SEQUENCE: 85
gttgcactgc aggctcaagc ggaggtgaag ctggatgaga ctgg                44

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 49

<400> SEQUENCE: 86
gttgcactgc aggctcaagc ggaggtaaag cttctcgagt ctgg                44

<210> SEQ ID NO 87
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 50

<400> SEQUENCE: 87
gttgcactgc aggctcaagc ggaaatgaga ctggtggaat ctgg                44

<210> SEQ ID NO 88
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 53

<400> SEQUENCE: 88
gttgcactgc aggctcaagc ggaagtgaag ctggtggagt ctga                44

<210> SEQ ID NO 89
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 64

-continued

<400> SEQUENCE: 89
gttgcactgc aggctcaagc gcaggttcag ctgcaacagt ctga                              44

<210> SEQ ID NO 90
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 66

<400> SEQUENCE: 90
gttgcactgc aggctcaagc ggagatccag ctgcagcagt ctgg                              44

<210> SEQ ID NO 91
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 67

<400> SEQUENCE: 91
gttgcactgc aggctcaagc ggaagtgatg ctggtggagt ctgg                              44

<210> SEQ ID NO 92
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 68

<400> SEQUENCE: 92
gttgcactgc aggctcaagc ggaggtgcag cctgttgagt ctgg                              44

<210> SEQ ID NO 93
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 69

<400> SEQUENCE: 93
gttgcactgc aggctcaagc ggacgtgaag catatggagt ctgg                              44

<210> SEQ ID NO 94
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 70

<400> SEQUENCE: 94
gttgcactgc aggctcaagc ggaagtgaag cttgaggagt ctgg                              44

<210> SEQ ID NO 95
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 71

<400> SEQUENCE: 95
gttgcactgc aggctcaagc ggaggtccag cttcagcagt cagg					44

<210> SEQ ID NO 96
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 73

<400> SEQUENCE: 96
gttgcactgc aggctcaagc gcaggtccag ctgcagcagt ctag					44

<210> SEQ ID NO 97
<211> LENGTH: 44
<212> TYPE: DNA
<213> ORGANISM: Artificial Sequence
<220> FEATURE:
<223> OTHER INFORMATION: Description of Artificial Sequence: Murine 5'
      heavy Chain Specific PCR Primer 74

<400> SEQUENCE: 97
gttgcactgc aggctcaagc gcaggtccag ctgcagcagt ctcg					44

<210> SEQ ID NO 98
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 75

<400> SEQUENCE: 98
gttgcactgc aggctcaagc ggaggttcag ctgcagcagt ctgt					44

<210> SEQ ID NO 99
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 124

<400> SEQUENCE: 99
gttgcactgc aggctcaagc gcaggtccaa ctgcagcagc ctgg					44

<210> SEQ ID NO 100
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 125

<400> SEQUENCE: 100
gttgcactgc aggctcaagc ggaggttcag ctgcagcagt ctgg					44

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 126

<400> SEQUENCE: 101
gttgcactgc aggctcaagc ggaggtccag ctgcaacaat ctgg					44

<210> SEQ ID NO 102
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 127

<400> SEQUENCE: 102
gttgcactgc aggctcaagc gcaggtccac gtgaagcagt ctgg                    44

<210> SEQ ID NO 103
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 204

<400> SEQUENCE: 103
gttgcactgc aggctcaagc ggatgtgcag cttcaggagt cggg                    44

<210> SEQ ID NO 104
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 205

<400> SEQUENCE: 104
gttgcactgc aggctcaagc gcaagttact ctaaaagagt ctgg                    44

<210> SEQ ID NO 105
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 207

<400> SEQUENCE: 105
gttgcactgc aggctcaagc ggaagtgcag ctgttggaga ctgg                    44

<210> SEQ ID NO 106
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 51

<400> SEQUENCE: 106
gttgcactgc aggctcaagc gcagatccag ttggtgcaat ctgg                    44

<210> SEQ ID NO 107
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 63

<400> SEQUENCE: 107
gttgcactgc aggctcaagc ggatgtgaac ttggaagtgt ctgg                    44

```
<210> SEQ ID NO 108
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 72

<400> SEQUENCE: 108
gttgcactgc aggctcaagc gcaggcttat ctacagcagt ctgg            44

<210> SEQ ID NO 109
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 206

<400> SEQUENCE: 109
gttgcactgc aggctcaagc gcaggtccaa gtgcagcagc ctgg            44

<210> SEQ ID NO 110
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 208

<400> SEQUENCE: 110
gttgcactgc aggctcaagc ggaagtgcag ctggtggaga ctgc            44

<210> SEQ ID NO 111
<211> LENGTH: 44
<212> TYPE: DNA
<213> ORGANISM: Artificial Sequence
<220> FEATURE:
<223> OTHER INFORMATION: Description of Artificial Sequence: Murine 5'
      Heavy Chain Specific PCR Primer 526

<400> SEQUENCE: 111
gttgcactgc aggctcaagc ggacgtgcag gtggtggagt ctgg            44

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Murine
      Heavy Chain Specific 3' PCR Primer 1

<400> SEQUENCE: 112 gatggggtg tcgttttggc                                        20

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Murine
      Heavy Chain Specific 3' PCR Primer 1170

<400> SEQUENCE: 113
ctggacaggg atccacagtt c                                     21
```